(12) United States Patent
Phull et al.

(10) Patent No.: US 11,390,637 B2
(45) Date of Patent: Jul. 19, 2022

(54) SALTS OF ANTIVIRAL PHOSPHONATE ANALOGUES AND PROCESS FOR PREPARATION THEREOF

(71) Applicant: CIPLA LIMITED, Mumbai (IN)

(72) Inventors: Manjinder Singh Phull, Mumbai (IN); Ashwini Amol Sawant, Mumbai (IN); Dharmaraj Ramachandra Rao, Thane (IN); Geena Malhotra, Mumbai (IN); Manish Gopaldas Gangrade, Mumbai (IN)

(73) Assignee: Cipla Limited, Mumbai (IN)

( * ) Notice: Subject to any disclaimer, the term of this patent is extended or adjusted under 35 U.S.C. 154(b) by 93 days.

(21) Appl. No.: 16/494,579

(22) PCT Filed: Mar. 16, 2018

(86) PCT No.: PCT/GB2018/050695
§ 371 (c)(1),
(2) Date: Sep. 16, 2019

(87) PCT Pub. No.: WO2018/167515
PCT Pub. Date: Sep. 20, 2018

(65) Prior Publication Data
US 2020/0131211 A1    Apr. 30, 2020

(30) Foreign Application Priority Data
Mar. 17, 2017    (IN) .............................. 201721009392

(51) Int. Cl.
*C07F 9/6561*    (2006.01)
(52) U.S. Cl.
CPC ................. *C07F 9/65616* (2013.01)
(58) Field of Classification Search
CPC .................................. C07F 9/65616
See application file for complete search history.

(56) References Cited

U.S. PATENT DOCUMENTS 9,227,990 B2 *    1/2016    Phull ....................... A61P 31/12

FOREIGN PATENT DOCUMENTS

| IN | 201721009392 | 3/2017 |
| WO | 2014068265 A1 | 5/2014 |
| WO | 2018167515 A1 | 9/2018 |

OTHER PUBLICATIONS

Berge et al., Journal of Pharmaceutical Sciences, Jan. 1977, vol. 66, No. 1, pp. 1-19. (Year: 1977).*
Chemical Abstracts Registry No. 1609111-13-8, indexed in the Registry file on STN CAS Online May 28, 2014. (Year: 2014).*
Chemical Abstracts Registry No. 1609111-19-4, indexed in the Registry file on STN CAS Online May 28, 2014. (Year: 2014).*
Chemical Abstracts Registry No. 1609111-17-2, indexed in the Registry file on STN CAS Online May 28, 2014. (Year: 2014).*
Foreign communication from a related application—International Search Report and the Written Opinion of the International Searching Authority, application No. PCT/GB2018/050695, dated May 7, 2018, 11 pages.
Foreign communication from a related application—International Preliminary Report on Patentability, application No. PCT/GB2018/050695, dated Sep. 17, 2019, 6 pages.

* cited by examiner

*Primary Examiner* — Laura L Stockton
(74) *Attorney, Agent, or Firm* — Conley Rose, P.C.; Rodney B. Carroll

(57) ABSTRACT

The present invention relates to certain acid salts of (((1-(6-amino-9H-purin-9-yl)propan-2-yloxy)methyl)(phenoxy)phosphoryloxy)methyl pivalate of Formula (I),

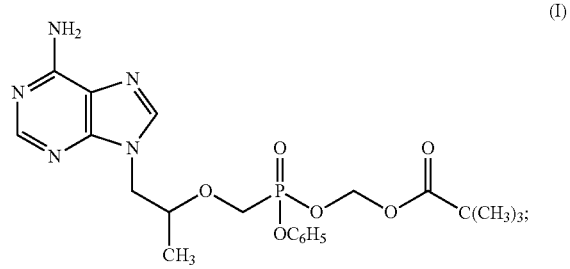

to processes for their preparation; to pharmaceutical compositions comprising such compounds, and methods of treating a disease which responds to inhibition of nucleotide reverse transcriptase activity.

21 Claims, 20 Drawing Sheets

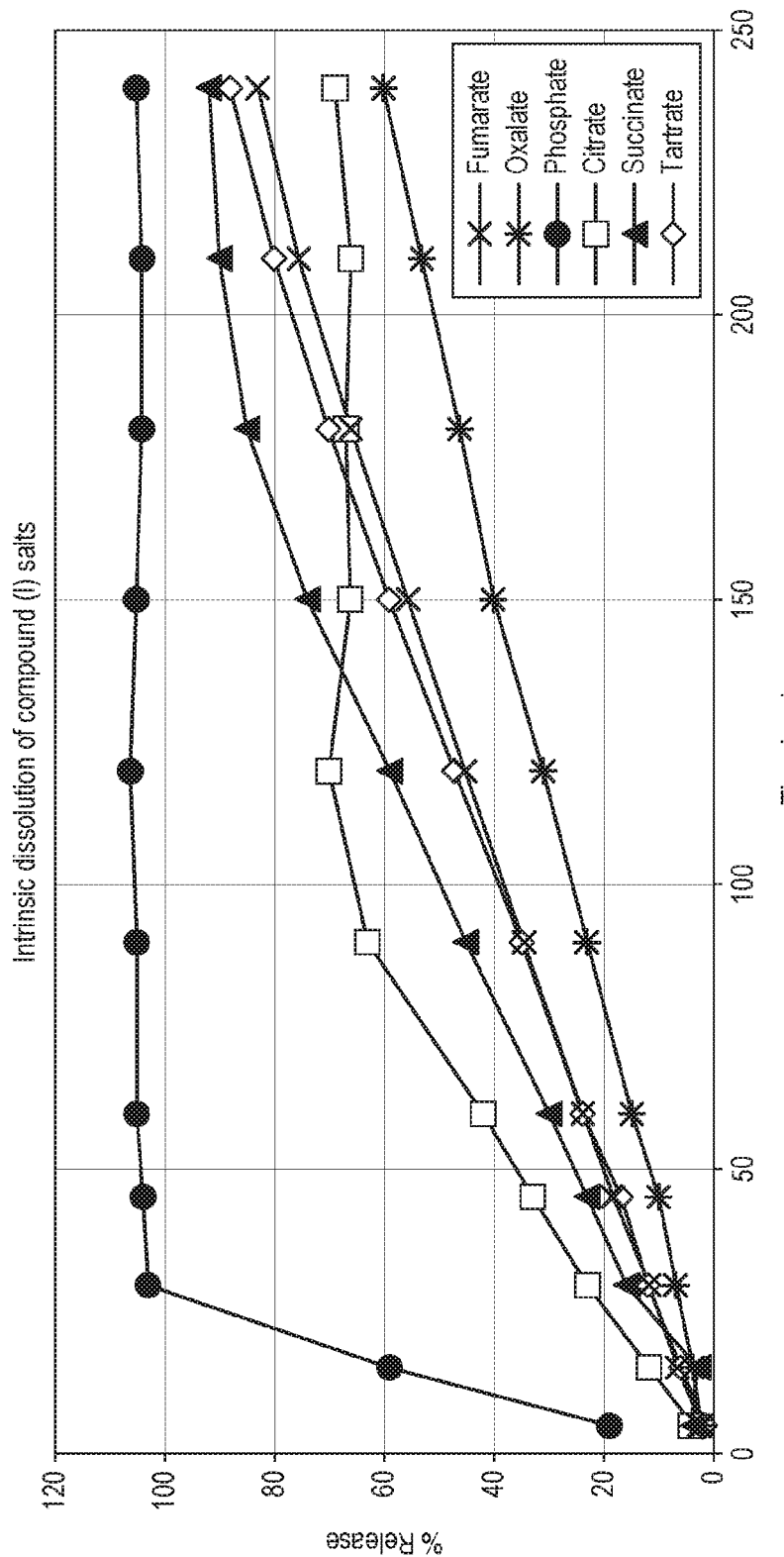

SALTS OF ANTIVIRAL PHOSPHONATE ANALOGUES AND PROCESS FOR PREPARATION THEREOF

CROSS REFERENCE TO RELATED APPLICATIONS

This application is a filing under 35 U.S.C. 371 of International Application No. PCT/GB2018/050695 filed Mar. 16, 2018, entitled "Salts of Antiviral Phosphonate Analogues and Process for Preparation Thereof" which claims priority to Indian Patent Application No. 201721009392 filed Mar. 17, 2017.

FIELD OF THE INVENTION

This invention relates to acid salts of (((1-(6-amino-9H-purin-9-yl)propan-2-yloxy)methyl)(phenoxy) phosphoryloxy)methyl pivalate, as well as to methods of making the same, pharmaceutical compositions comprising the same and methods of treatment using the same.

RELATED BACKGROUND ART

The compound (((1-(6-amino-9H-purin-9-yl)propan-2-yloxy)methyl)(phenoxy) phosphoryloxy)methyl pivalate of Formula (I) is disclosed in WO 2014/068265.

Formula (I)

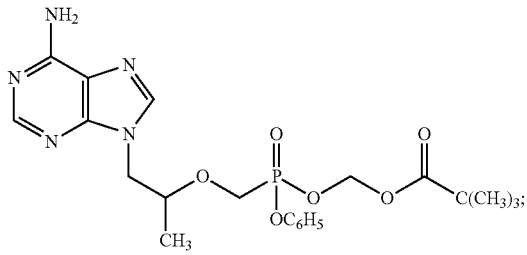

Valuable pharmacological properties are attributed to this compound. It can be used, for example, as a nucleotide reverse transcriptase inhibitor useful in therapy for diseases which respond to inhibition of protein kinase activity.

New or improved forms of existing nucleotide reverse transcriptase inhibitors are continually needed for developing new, improved and more effective pharmaceutical formulations for the treatment of cancer and other diseases. The salt forms and methods of preparing the salt forms described herein are directed toward these needs and other ends.

SUMMARY OF THE INVENTION

The present invention is directed to inter alia acid salts of (((1-(6-amino-9H-purin-9-yl)propan-2-yloxy)methyl) (phenoxy) phosphoryloxy) methyl pivalate.

In one aspect, the present invention provides an acid salt of (((1-(6-amino-9H-purin-9-yl)propan-2-yloxy)methyl) (phenoxy) phosphoryloxy) methyl pivalate selected from:

(((1-(6-amino-9H-purin-9-yl)propan-2-yloxy) methyl) (phenoxy) phosphoryloxy) methyl pivalate phosphoric acid salt (phosphate salt);

(((1-(6-amino-9H-purin-9-yl)propan-2-yloxy) methyl) (phenoxy) phosphoryloxy) methyl pivalate oxalic acid salt (oxalate salt);

(((1-(6-amino-9H-purin-9-yl)propan-2-yloxy) methyl) (phenoxy) phosphoryloxy) methyl pivalate succinic acid salt (succinate salt);

(((1-(6-amino-9H-purin-9-yl)propan-2-yloxy) methyl) (phenoxy) phosphoryloxy) methyl pivalate citric acid salt (citrate salt);

or a solvate or hydrate thereof.

In certain aspects, the acid salts of (((1-(6-amino-9H-purin-9-yl)propan-2-yloxy)methyl) (phenoxy) phosphoryloxy) methyl pivalate of the present invention may be in solvated form. Examples of solvated forms include, but are not limited to, solvates formed with ethanol, tetrahydrofuran, diethyl ether, acetone and/or water (i.e. a hydrate). Thus, in the context of the present invention the term "solvate" includes hydrates.

In another aspect, the present invention provides (((1-(6-amino-9H-purin-9-yl)propan-2-yloxy) methyl) (phenoxy) phosphoryloxy) methyl pivalate tartaric acid salt (tartrate salt), or a solvate or hydrate thereof, having an XRD pattern comprising peaks at about 4.73 and 20.65°2θ±0.2°2θ.

In yet a further aspect, the present invention provides (((1-(6-amino-9H-purin-9-yl)propan-2-yloxy) methyl) (phenoxy) phosphoryloxy) methyl pivalate fumaric acid salt (fumarate salt), or a solvate or hydrate thereof, having an XRD pattern comprising peaks at about 5.03, 23.59 and 29.02°2θ±0.2°2θ.

In certain aspects, the acid salts of (((1-(6-amino-9H-purin-9-yl)propan-2-yloxy)methyl) (phenoxy) phosphoryloxy) methyl pivalate of the present invention may be in substantially crystalline or amorphous form. The number of solvent molecules in the crystalline or amorphous structure of the salt is not limited and can, for example, be in the range of from about 0.1 to about 7 mole of solvent per mole of (((1-(6-amino-9H-purin-9-yl)propan-2-yloxy)methyl) (phenoxy) phosphoryloxy) methyl pivalate.

In another aspect of the present invention, the acid salts of (((1-(6-amino-9H-purin-9-yl)propan-2-yloxy)methyl) (phenoxy) phosphoryloxy) methyl pivalate may be in desolvated form.

The present invention also provides one or more of polymorphic forms of acid salts of (((1-(6-amino-9H-purin-9-yl)propan-2-yloxy)methyl) (phenoxy) phosphoryloxy) methyl pivalate.

The present invention is further directed to a process of preparing a variety of crystalline acid salts of (((1-(6-amino-9H-purin-9-yl)propan-2-yloxy)methyl) (phenoxy) phosphoryloxy) methyl pivalate comprising the steps of: reacting (((1-(6-amino-9H-purin-9-yl)propan-2-yloxy)methyl) (phenoxy) phosphoryloxy) methyl pivalate free base with an acid selected from fumaric acid, tartaric acid, phosphoric acid, oxalic acid, succinic acid or citric acid, in a suitable solvent, and thereafter optionally isolating the acid addition salt so formed.

The invention is further directed to pharmaceutical compositions comprising:
(a) an acid salt of (((1-(6-amino-9H-purin-9-yl)propan-2-yloxy)methyl) (phenoxy) phosphoryloxy) methyl pivalate (which may be present in crystalline or amorphous form), or solvate or hydrate thereof and
(b) at least one pharmaceutically acceptable excipient.

The present invention is also directed to a method of treating a disease which responds to an inhibition of nucleotide reverse transcriptase activity, such as HIV and/or AIDS, comprising the step of administering to a subject in need of such treatment a therapeutically effective amount of an acid salt of (((1-(6-amino-9H-purin-9-yl)propan-2-yloxy) methyl) (phenoxy) phosphoryloxy) methyl pivalate) or a solvate or hydrate thereof.

BRIEF DESCRIPTION OF THE DRAWINGS

FIG. 20 shows intrinsic dissolution data for various acid salts of (((1-(6-amino-9H-purin-9-yl)propan-2-yloxy) methyl) (phenoxy) phosphoryloxy) methyl pivalate.

DETAILED DESCRIPTION OF THE INVENTION

Figure 1:
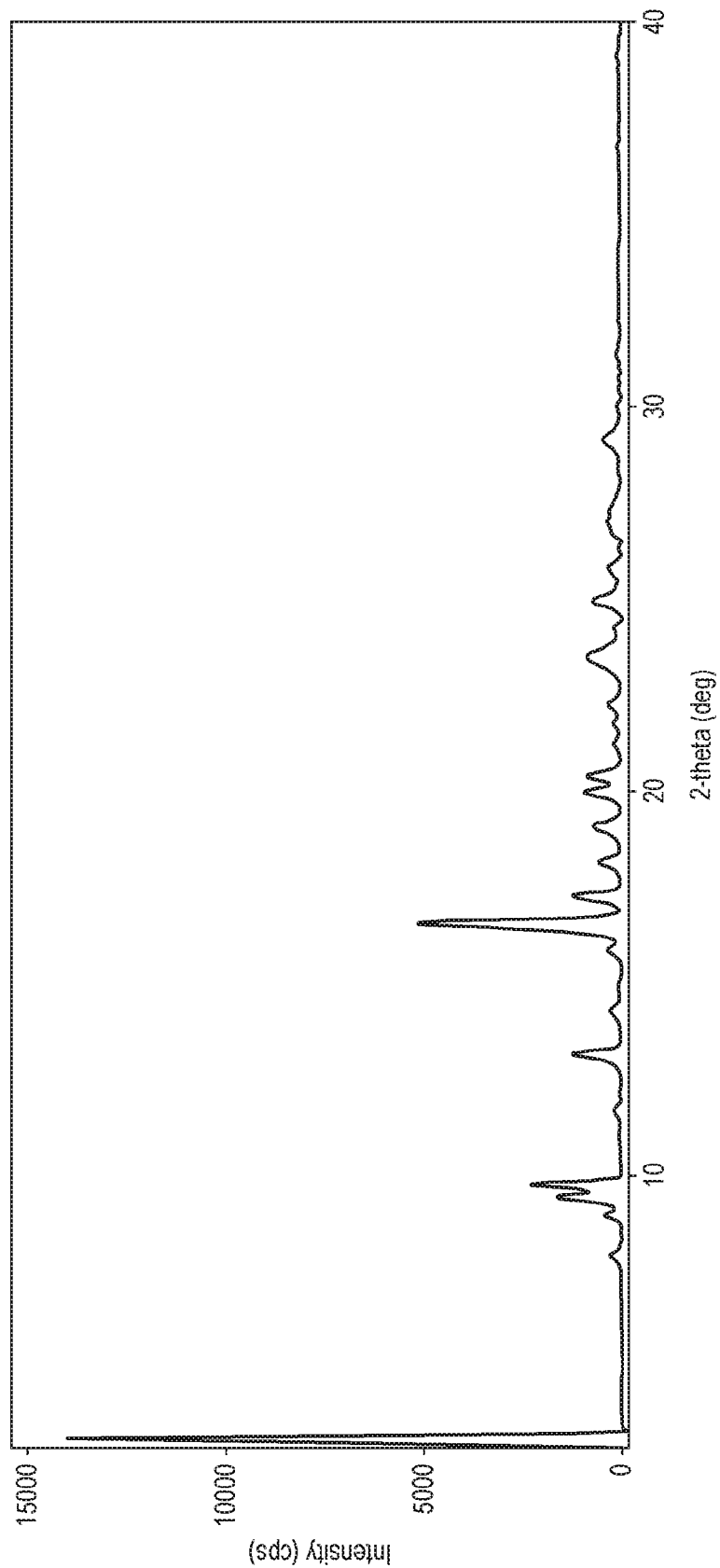
FIG. 1 shows the X-ray powder diffraction patterns (XRDs) for Form I of the phosphate salt of (((1-(6-amino-9H-purin-9-yl)propan-2-yloxy)methyl) (phenoxy) phosphoryloxy) methyl pivalate.

The present invention provides, inter alia, acid salts of the nucleotide reverse transcriptase inhibitor (((1-(6-amino-9H-purin-9-yl)propan-2-yloxy)methyl) (phenoxy) phosphoryloxy) methyl pivalate selected from the group comprising the phosphoric acid salt, oxalic acid salt, succinic acid salt and citric acid salt, or a solvate or hydrate thereof.

These salts modulate the activity of one or more nucleotide reverse transcriptase and are useful, for example, in the treatment of diseases associated with nucleotide reverse transcriptase expression or activity, such as acquired immune deficiency syndrome (AIDS) and/or an HIV infection.

The salts of the invention have numerous advantageous properties over the free base form. In particular, these salts are highly crystalline which would facilitate the preparation of pharmaceutical formulations and improve general handling, manipulation, and storage of the active ingredient. The salts of the invention also have superior aqueous solubility, rate of dissolution, chemical stability (with a longer shelf life), compatibility with excipients, and reproducibility compared with the free base form.

The compound (((1-(6-amino-9H-purin-9-yl)propan-2-yloxy)methyl) (phenoxy) phosphoryloxy) methyl pivalate of formula (I) may exist as a diastereomer having either the (R,R), (S,S), (R,S) or (S,R) configuration. Preferably, the compound of formula (I) or the acid salt thereof is in the form of the (R,R) diastereomer. Accordingly, salts of the present invention also include all diastereomers occurring in the salts.

Salts of the present invention also include all isotopes of atoms occurring in the salts. Isotopes include those atoms having the same atomic number but different mass numbers. For example, isotopes of hydrogen include tritium and deuterium.

The acid salts of the present invention may be prepared by combining in solution the free base compound of Formula (I) and an acid containing the anion of the salt form desired, and then optionally isolating the solid salt product from the reaction solution by known methods, including, but not limited to crystallization and/or precipitation and/or evaporation and the like. Other salt-forming techniques are known in the art and can be employed as alternative methods.

The use of certain solvents during the aforementioned process has been found to produce different polymorphic forms of the acid salts of (((1-(6-amino-9H-purin-9-yl)propan-2-yloxy)methyl) (phenoxy) phosphoryloxy) methyl pivalate of formula (I), which may exhibit one or more favourable characteristics described above. The processes for the preparation of the polymorphs described herein, and characterization of these polymorphs are described in greater detail below.

As polymorphic forms are reliably characterized by peak positions in the X-ray diffractogram, the polymorphs of the present invention have been characterized by powder X-ray diffraction spectroscopy which produces a fingerprint of the particular crystalline form.

In one aspect, the pharmaceutically acceptable acid addition salt of the (((1-(6-amino-9H-purin-9-yl)propan-2-yloxy) methyl) (phenoxy) phosphoryloxy) methyl pivalate of Formula (I) is phosphoric acid salt of formula (Ia).

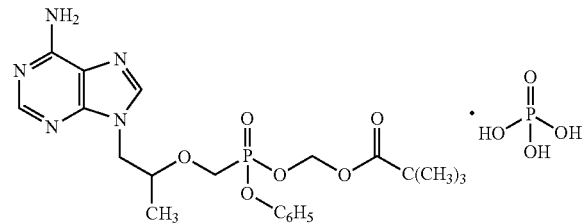

Formula I. Phosphoric acid

The phosphate salt according to the present invention is a 1:1 salt of phosphoric acid with (((1-(6-amino-9H-purin-9-yl)propan-2-yloxy) methyl) (phenoxy) phosphoryloxy) methyl pivalate. Thus phosphate salt is monophosphate salt of formula (Ia).

In a further aspect, the present invention relates to a process for preparing (((1-(6-amino-9H-purin-9-yl)propan-2-yloxy) methyl) (phenoxy) phosphoryloxy) methyl pivalate phosphoric acid salt of formula (Ia), which comprises reacting the free base of a (((1-(6-amino-9H-purin-9-yl)propan-2-yloxy) methyl) (phenoxy) phosphoryloxy) methyl pivalate of Formula (I) with phosphoric acid.

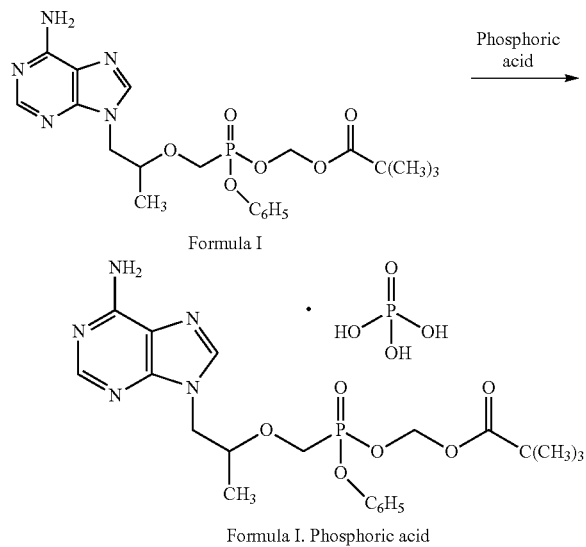

Formula I. Phosphoric acid

The phosphate salt according to the invention is characterised by good crystallinity and low amorphisation during grinding and compression. In addition, it is not hygroscopic and is readily soluble in physiologically acceptable solvents.

In another aspect, the present invention provides crystalline polymorphic form of (((1-(6-amino-9H-purin-9-yl)propan-2-yloxy) methyl) (phenoxy) phosphoryloxy) methyl pivalate phosphoric acid salt of formula (Ia) hereinafter referred to as Form I.

In one aspect, Form I is characterized by an X-ray powder diffraction pattern comprising the following 2θ values measured on a Rigaku, MiniFlex 2, tabletop X-ray powder diffractometer using CuKα, radiation.

In an aspect, Form I is characterized by having an XRD pattern comprising peaks at 3.25 and 16.58°2θ±0.2°2θ. The XRD pattern may comprise further peaks at 9.80 and 23.34°2θ±0.2°2θ. The XRD pattern may comprise still further peaks at 9.5 13.2, 17.26, 19.09, 24.84 and 29.16°2θ±0.2°2θ.

In one aspect, Form I has an XRD pattern substantially as shown in FIG. 1.

In one aspect, Form I has an XRD pattern with peaks at 2θ-values as shown in Table 1.

TABLE 1

| Diffraction angle (2θ-values) | Intensity (%) |
| --- | --- |
| 3.25 | 100.0 |
| 9.50 | 14.79 |
| 9.80 | 20.23 |
| 13.2 | 13.03 |
| 16.58 | 57.63 |
| 17.26 | 11.94 |
| 19.09 | 10.19 |
| 23.34 | 22.63 |
| 24.84 | 19.12 |
| 29.16 | 11.66 |

Crystalline Form I may also be characterized by having an IR spectrum comprising characteristic peaks at about 2974 $cm^{-1}$, 1750 $cm^{-1}$, 1703 $cm^{-1}$, 1612 $cm^{-1}$, 1591 $cm^{-1}$, 1518 $cm^{-1}$, 1489 $cm^{-1}$, 1414 $cm^{-1}$, 1266 $cm^{-1}$, 1236 $cm^{-1}$, 1199 $cm^{-1}$, 1130 $cm^{-1}$, 1079 $cm^{-1}$, 1049 $cm^{-1}$, 1018 $cm^{-1}$, 986 $cm^{-1}$, 928 $cm^{-1}$, 885 $cm^{-1}$, 760 $cm^{-1}$, 717 $cm^{-1}$, and 687 $cm^{-1}$±2 $cm^{-1}$.

Figure 2:
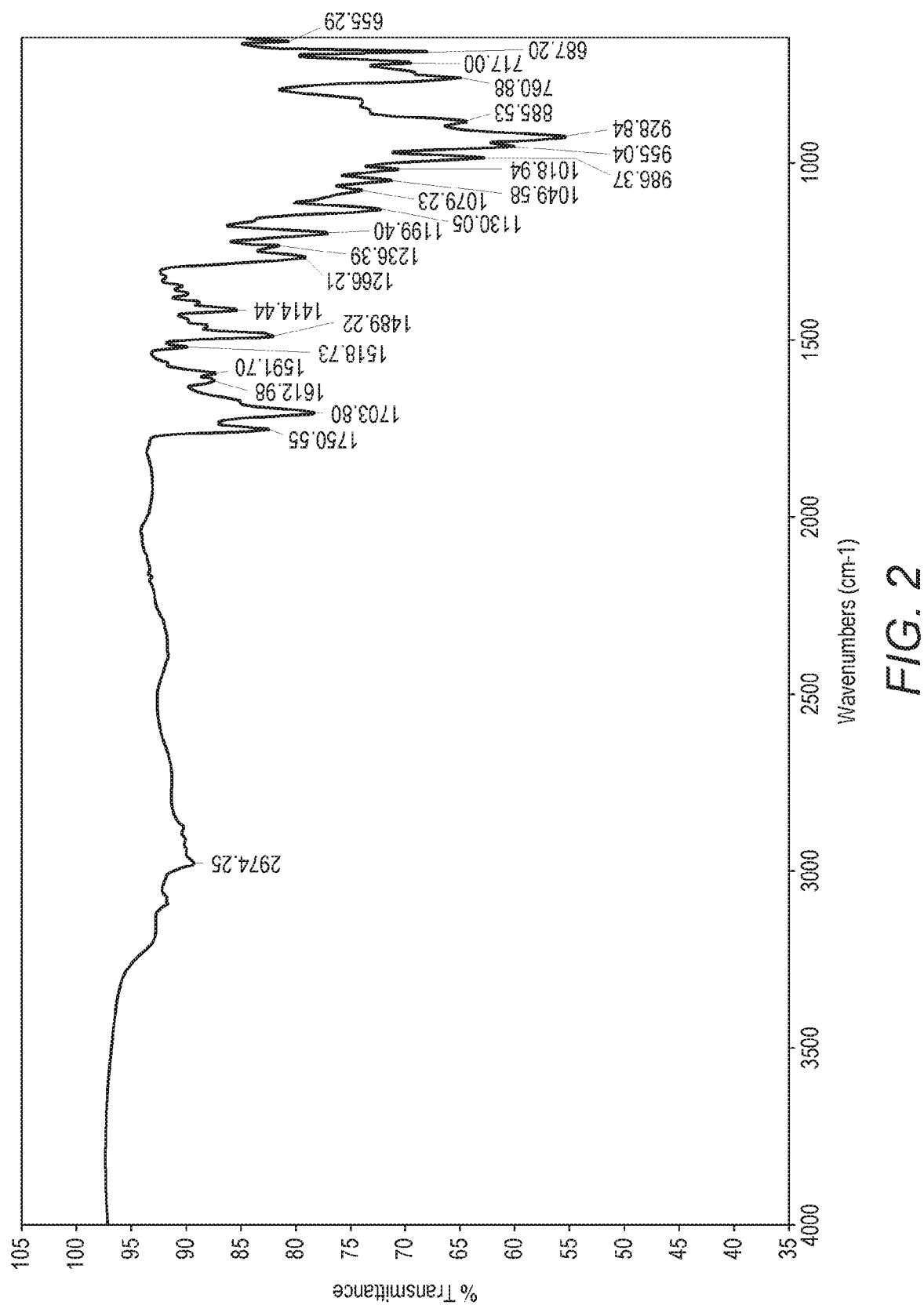
FIG. 2 shows an Infra-Red (IR) absorption spectrum for Form I of the phosphate salt of (((1-(6-amino-9H-purin-9-yl)propan-2-yloxy)methyl) (phenoxy) phosphoryloxy) methyl pivalate.

In one aspect, Form I has an IR spectrum substantially as shown in FIG. 2.

Crystalline Form I may also be characterized as having a DSC spectrum exhibiting a (exothermic) significant peak between about 133° C. and about 136° C., preferably exhibiting a peak at about 133° C.

Figure 3:
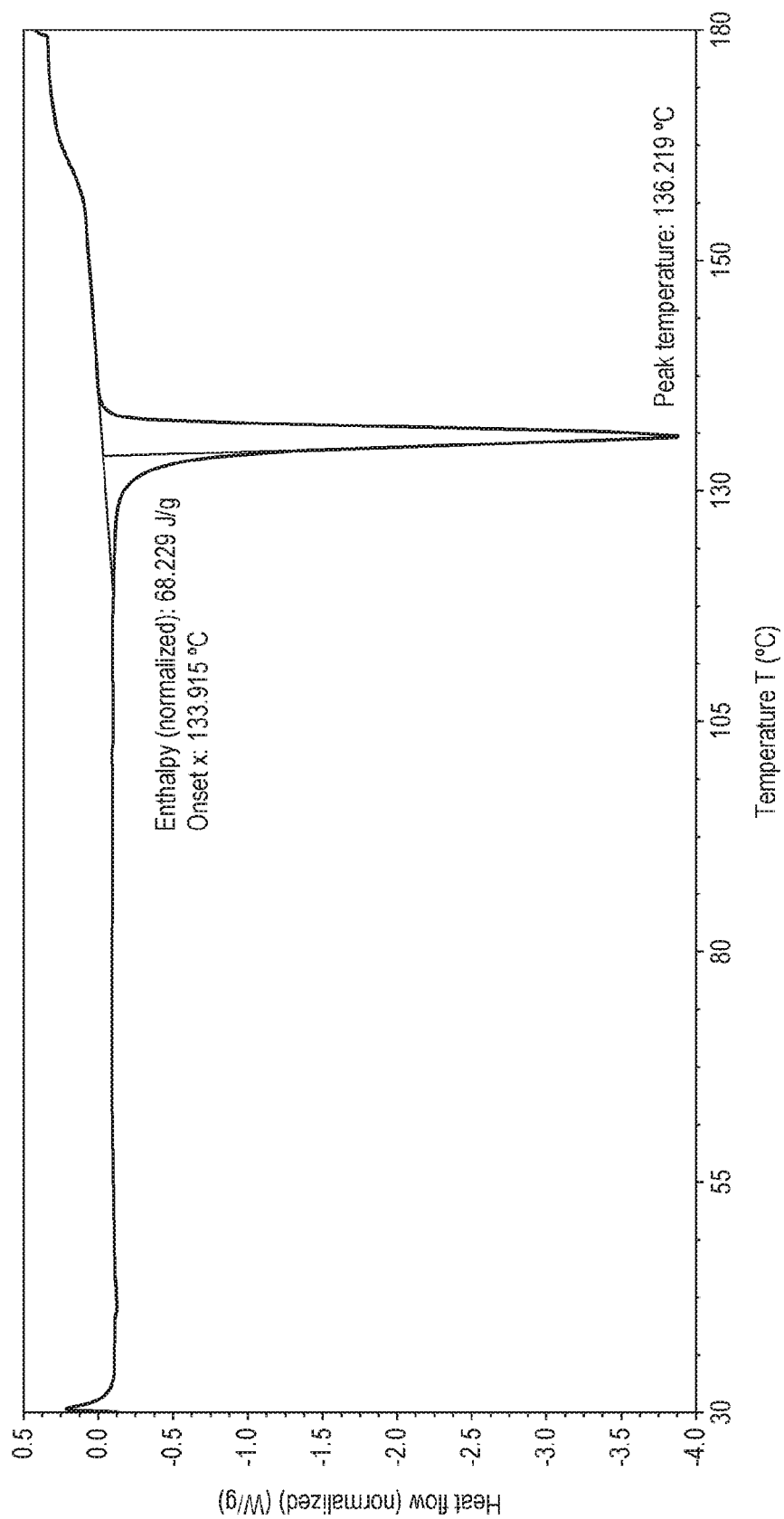
FIG. 3 differential scanning calorimetry (DSC) graph for Form I of the phosphate salt of (((1-(6-amino-9H-purin-9-yl)propan-2-yloxy)methyl) (phenoxy) phosphoryloxy) methyl pivalate.

In another aspect, Form I has a differential scanning calorimetry (DSC) thermogram substantially as shown in FIG. 3.

Those skilled in the art would recognize that Form I may be further characterized by other known analytical and/or spectroscopic methods including, but not limited to thermogravimetric analysis (TGA), dynamic vapor sorption (DVS), solid state NMR and Raman spectroscopy.

In another aspect, the pharmaceutically acceptable acid addition salt of the (((1-(6-amino-9H-purin-9-yl)propan-2-yloxy) methyl) (phenoxy) phosphoryloxy) methyl pivalate of Formula (I) is oxalic acid salt of formula (Ib).

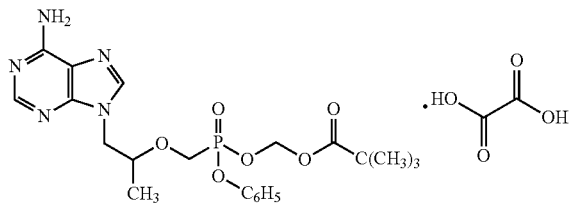

Formula I. Oxalic acid

The oxalate salt according to the present invention is a 1:1 salt of oxalic acid with (((1-(6-amino-9H-purin-9-yl)propan-2-yloxy) methyl) (phenoxy) phosphoryloxy) methyl pivalate. Thus oxalate salt is mono oxalate salt of formula (Ib).

In a further aspect, the present invention relates to a process for preparing (((1-(6-amino-9H-purin-9-yl)propan-2-yloxy) methyl) (phenoxy) phosphoryloxy) methyl pivalate oxalic acid salt of formula (Ib), which comprises reacting the free base of a (((1-(6-amino-9H-purin-9-yl)propan-2-yloxy) methyl) (phenoxy) phosphoryloxy) methyl pivalate of Formula (I) with oxalic acid.

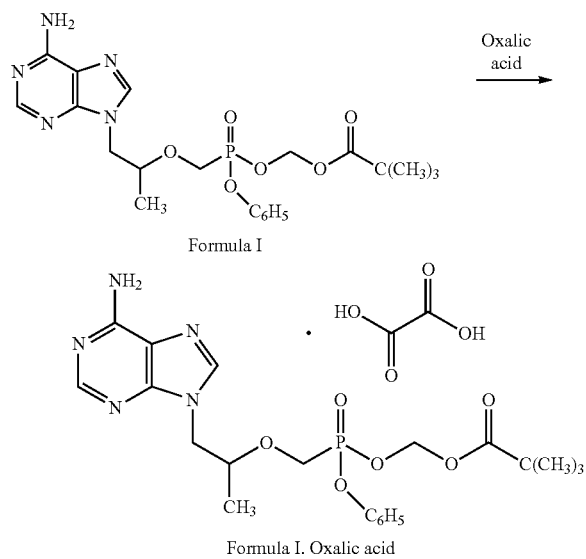

Formula I. Oxalic acid

The oxalate salt according to the invention is characterised by good crystallinity and low amorphisation during grinding and compression. In addition, it is not hygroscopic and is readily soluble in physiologically acceptable solvents.

In another aspect, the present invention provides crystalline polymorphic form of (((1-(6-amino-9H-purin-9-yl)propan-2-yloxy) methyl) (phenoxy) phosphoryloxy) methyl pivalate oxalic acid salt of formula (Ib), hereinafter referred to as Form II.

In one aspect, Form II is characterized by an X-ray powder diffraction pattern comprising the following 2θ values measured on a Rigaku, MiniFlex 2, tabletop X-ray powder diffractometer using CuKα, radiation.

In one aspect, Form II is characterized by having an XRD pattern comprising peaks at 4.16, 21.30 and 25.7°2θ±0.2°2θ. The XRD pattern may comprise further peaks at 15.65, 17.00, 17.70, 19.35, 23.15, and 30.12°2θ±0.2°2θ.

Figure 4:
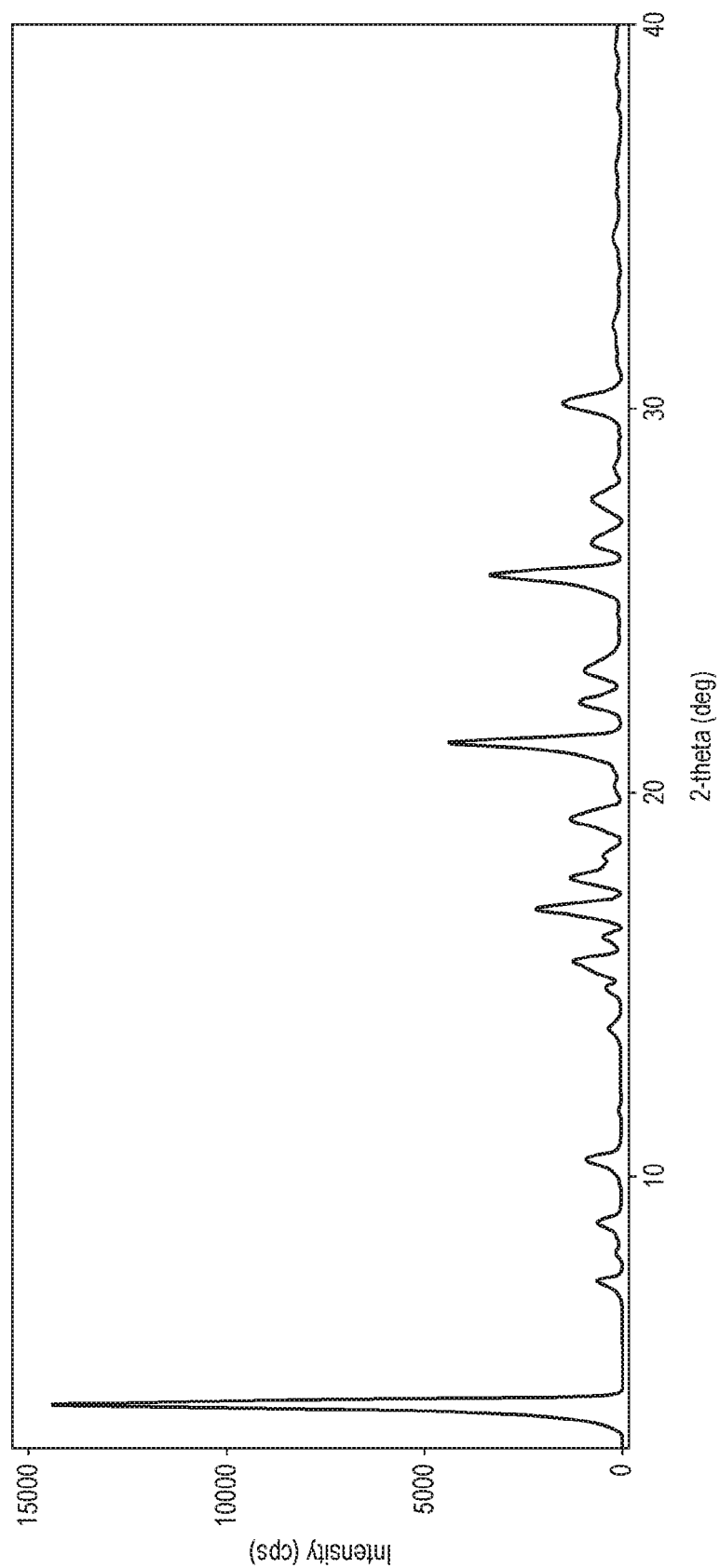
FIG. 4 shows the x-ray powder diffraction patterns (XRDs) for Form II of the oxalate salt of (((1-(6-amino-9H-purin-9-yl)propan-2-yloxy)methyl) (phenoxy) phosphoryloxy) methyl pivalate

In one aspect, Form II has an XRD pattern substantially as shown in FIG. 4.

In another aspect, Form II has an XRD pattern with peaks at 2θ-values as shown in Table 2.

TABLE 2

| Diffraction angle (2θ-values) | Intensity (%) |
|---|---|
| 4.16 | 100.0 |
| 15.65 | 12.43 |
| 17.00 | 18.10 |
| 17.70 | 14.63 |
| 19.35 | 12.76 |
| 23.15 | 11.04 |
| 25.7 | 32.84 |
| 30.12 | 17.37 |

Crystalline Form II may also be characterized by having an IR spectrum comprising characteristic IR spectra peaks at about 3088 cm$^{-1}$, 3185 cm$^{-1}$, 2979 cm$^{-1}$, 1735 cm$^{-1}$, 1693 cm$^{-1}$, 1596 cm$^{-1}$, 1512 cm$^{-1}$, 1491 cm$^{-1}$, 1455 cm$^{-1}$, 1411 cm$^{-1}$, 1368 cm$^{-1}$, 1350 cm$^{-1}$, 1264 cm$^{-1}$, 1229 cm$^{-1}$, 1202 cm$^{-1}$, 1137 cm$^{-1}$, 1071 cm$^{-1}$, 1024 cm$^{-1}$, 994 cm$^{-1}$, 908 cm$^{-1}$, 885 cm$^{-1}$, 820 cm$^{-1}$, 765 cm$^{-1}$, 748 cm$^{-1}$, 716 cm$^{-1}$, 704 cm$^{-1}$, and 689 cm$^{-1}$±2 cm$^{-1}$.

Figure 5:
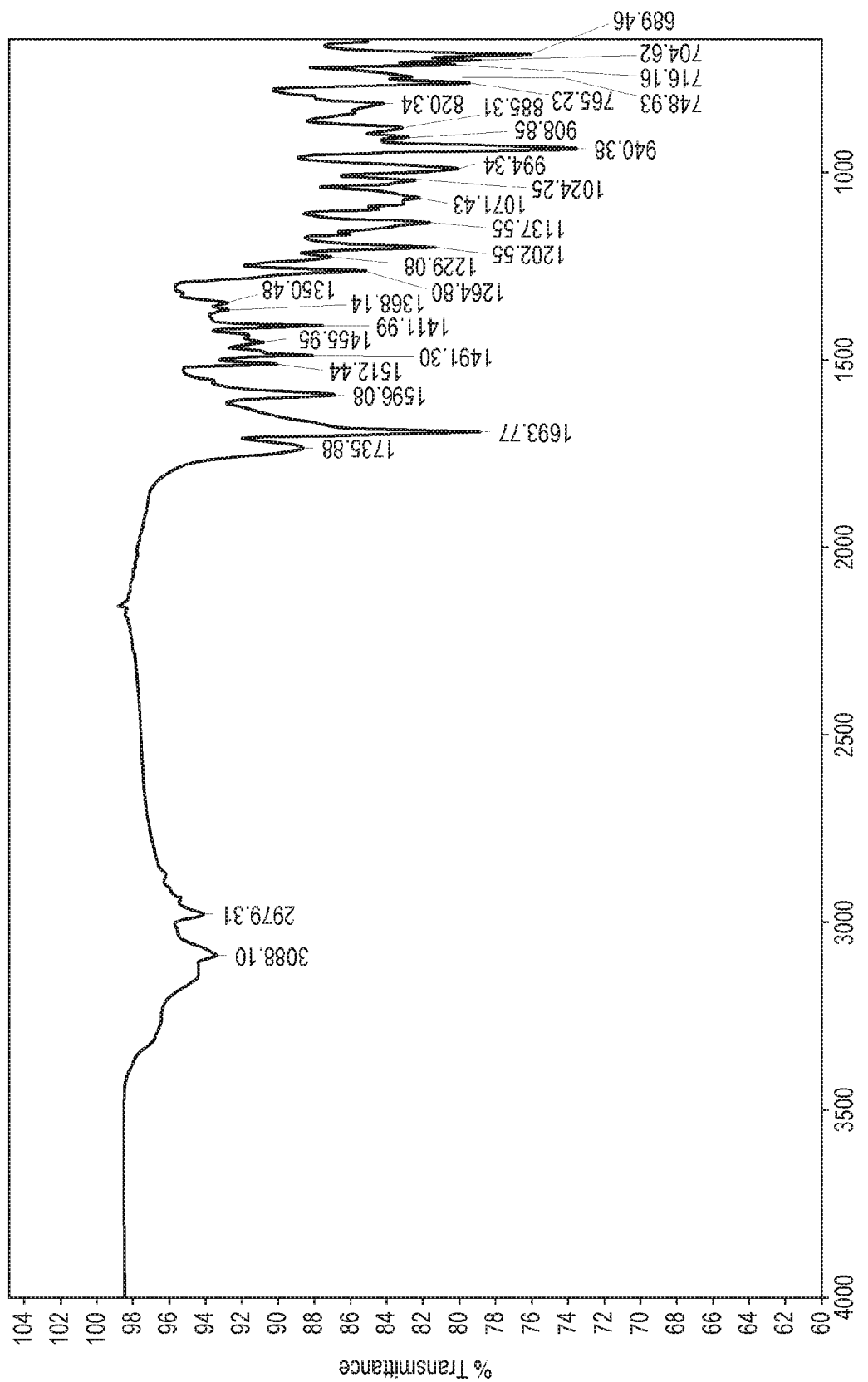
FIG. 5 shows an Infra-Red (IR) absorption spectrum for Form II of the oxalate salt of (((1-(6-amino-9H-purin-9-yl) propan-2-yloxy)methyl) (phenoxy) phosphoryloxy) methyl pivalate.

In one aspect, Form II exhibits an IR spectrum pattern substantially as shown in FIG. 5.

Form II may also be characterized as having a DSC spectrum exhibiting a (exothermic) significant peak between about 164° C. and about 168° C., preferably exhibiting a peak at about 164.9° C.

Figure 6:
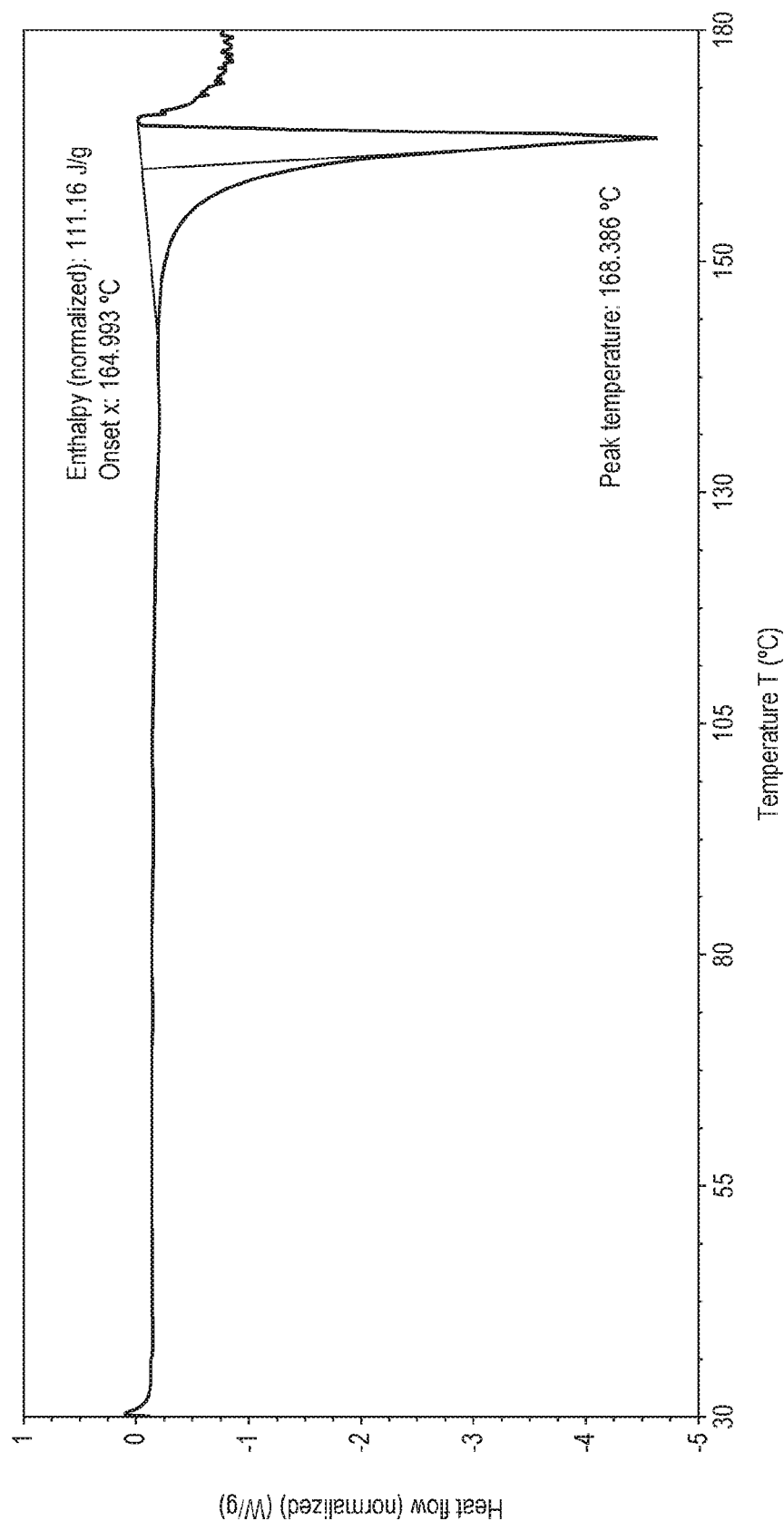
FIG. 6 differential scanning calorimetry (DSC) graph for Form II of the oxalate salt of (((1-(6-amino-9H-purin-9-yl) propan-2-yloxy)methyl) (phenoxy) phosphoryloxy) methyl pivalate.

In another aspect, crystalline Form II may exhibit a differential scanning calorimetry (DSC) thermogram substantially as shown in FIG. 6

Those skilled in the art would recognize that Form II may be further characterized by other known analytical and/or spectroscopic methods including, but not limited to thermogravimetric analysis (TGA), dynamic vapor sorption (DVS), solid state NMR and Raman spectroscopy.

In another aspect, the pharmaceutically acceptable acid addition salt of the (((1-(6-amino-9H-purin-9-yl)propan-2-yloxy) methyl) (phenoxy) phosphoryloxy) methyl pivalate of Formula (I) is succinic acid salt of formula (Ic).

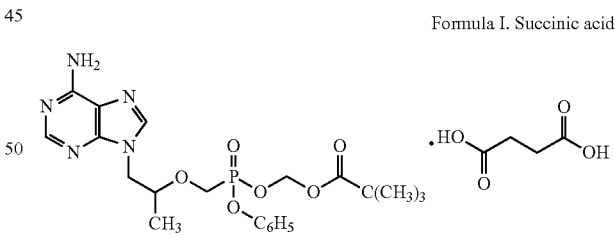

Formula I. Succinic acid

The succinate salt according to the present invention is a 1:1 salt of succinic acid with (((1-(6-amino-9H-purin-9-yl) propan-2-yloxy) methyl) (phenoxy) phosphoryloxy) methyl pivalate. Thus succinate salt is mono succinate salt of formula (Ic).

In a further aspect, the present invention relates to a process for preparing (((1-(6-amino-9H-purin-9-yl)propan-2-yloxy) methyl) (phenoxy) phosphoryloxy) methyl pivalate succinic acid salt of formula (Ic), which comprises reacting the free base of a (((1-(6-amino-9H-purin-9-yl)propan-2-yloxy) methyl) (phenoxy) phosphoryloxy) methyl pivalate of Formula (I) with succinic acid.

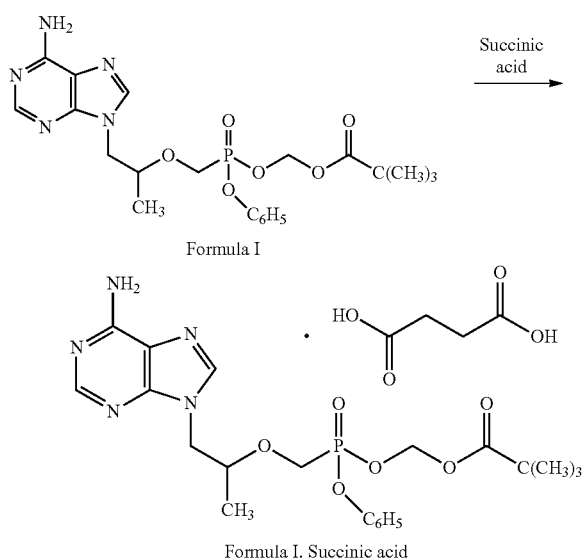

Formula I

Formula I. Succinic acid

The succinate salt according to the invention is characterised by good crystallinity and low amorphisation during grinding and compression. In addition, it is not hygroscopic and is readily soluble in physiologically acceptable solvents.

In another aspect, the present invention provides crystalline polymorphic form of (((1-(6-amino-9H-purin-9-yl)propan-2-yloxy) methyl) (phenoxy) phosphoryloxy) methyl pivalate succinic acid salt of formula (Ic), hereinafter referred to as Form III.

The crystalline Form III may be characterized by an X-ray powder diffraction pattern comprising the following 2θ values measured on a Rigaku, MiniFlex 2, tabletop X-ray powder diffractometer using CuKα, radiation.

Form III is characterized by having an XRD pattern comprising peaks at 5.07, 19.2, 20.2, 22.40, and 24.8°2θ±0.2°2θ. The XRD pattern may comprise further peaks at 15.83, 26.20, 27.87 and 30.12°2θ±0.2°2θ. The XRD pattern comprise still further peaks at 10.10, 11.67, 15.07, 17.90, 18.31, 21.55 and 23.22°2θ±0.2°2θ.

Figure 7:
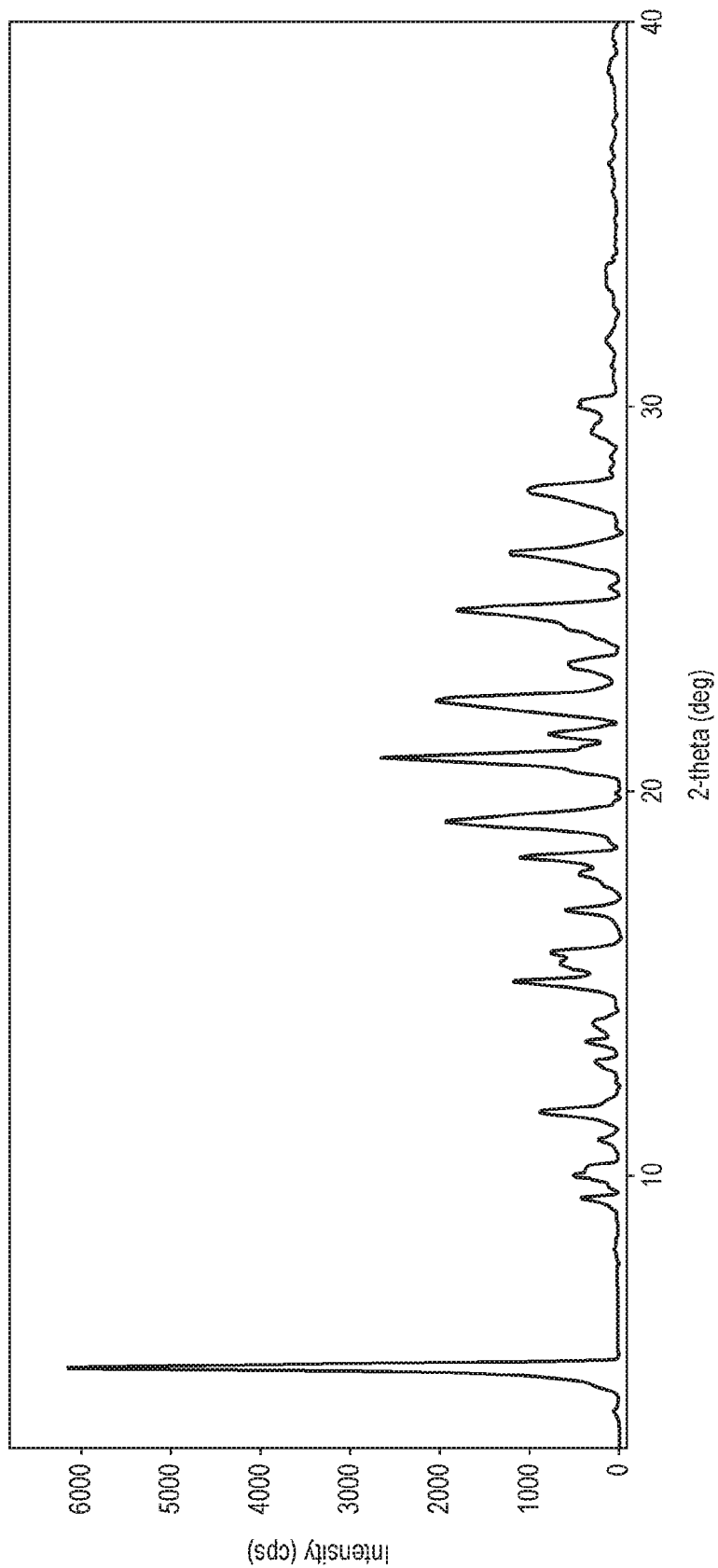
FIG. 7 shows the x-ray powder diffraction patterns (XRDs) for Form III of the succinate salt of (((1-(6-amino-9H-purin-9-yl)propan-2-yloxy)methyl) (phenoxy) phosphoryloxy) methyl pivalate.

In one aspect, Form III has an XRD pattern substantially as shown in FIG. 7.

In another aspect, Form III has an XRD pattern with peaks at 2θ-values as shown in Table 3.

TABLE 3

| Diffraction angle (2θ-values) | Intensity (%) |
|---|---|
| 5.07 | 100.0 |
| 10.10 | 14.30 |

TABLE 3-continued

| Diffraction angle (2θ-values) | Intensity (%) |
|---|---|
| 11.67 | 19.06 |
| 15.07 | 15.84 |
| 15.83 | 34.87 |
| 17.90 | 11.43 |
| 18.31 | 18.26 |
| 19.2 | 55.57 |
| 20.2 | 66.14 |
| 21.55 | 14.12 |
| 22.40 | 66.17 |
| 23.22 | 11.97 |
| 24.8 | 61.21 |
| 26.20 | 36.46 |
| 27.87 | 34.12 |
| 30.12 | 30.49 |

Crystalline Form III may also be characterized by having an IR spectrum comprising characteristic IR spectra peaks at about 3331 cm$^{-1}$, 3165 cm$^{-1}$, 2976 cm$^{-1}$, 1751 cm$^{-1}$, 1664 cm$^{-1}$, 1618 cm$^{-1}$, 1488 cm$^{-1}$, 1418 cm$^{-1}$, 1397 cm$^{-1}$, 1316 cm$^{-1}$, 1273 cm$^{-1}$, 1194 cm$^{-1}$, 1134 cm$^{-1}$, 1097 cm$^{-1}$, 1067 cm$^{-1}$, 1019 cm$^{-1}$, 986 cm$^{-1}$, 931 cm$^{-1}$, 892 cm$^{-1}$, 827 cm$^{-1}$, 796 cm$^{-1}$, 719 cm$^{-1}$, and 688 cm$^{-1}$±2 cm$^{-1}$.

Figure 8:
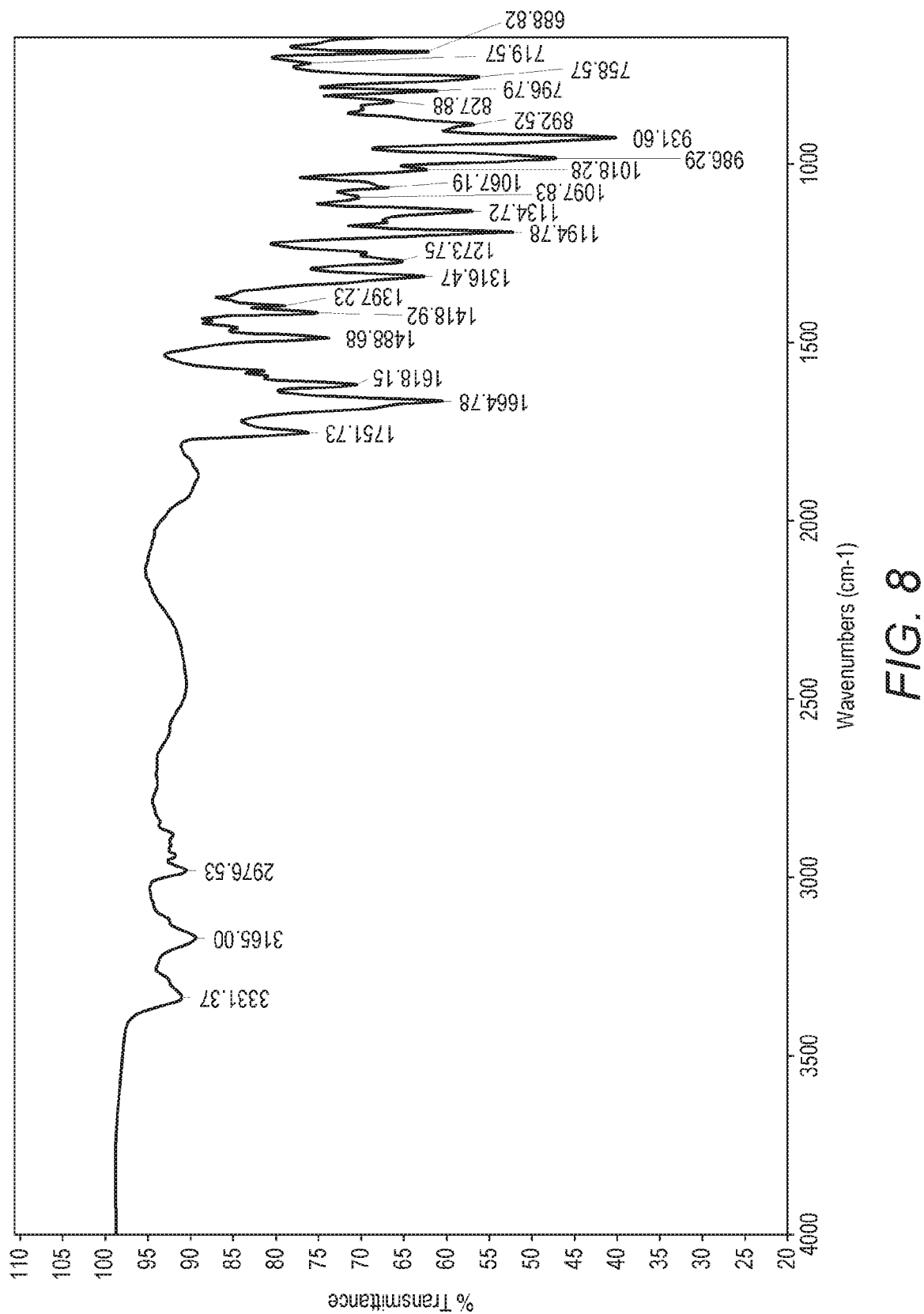
FIG. 8 shows an Infra-Red (IR) absorption spectrum for Form III of the succinate salt of (((1-(6-amino-9H-purin-9-yl)propan-2-yloxy)methyl) (phenoxy) phosphoryloxy) methyl pivalate.

In one aspect, Form III may exhibit an IR spectrum pattern substantially as shown in FIG. 8.

Form III may also be characterized as having a DSC spectrum exhibiting a (exothermic) significant peak between about 137° C. and about 143° C., preferably exhibiting a peak at about 137.2° C.

Figure 9:
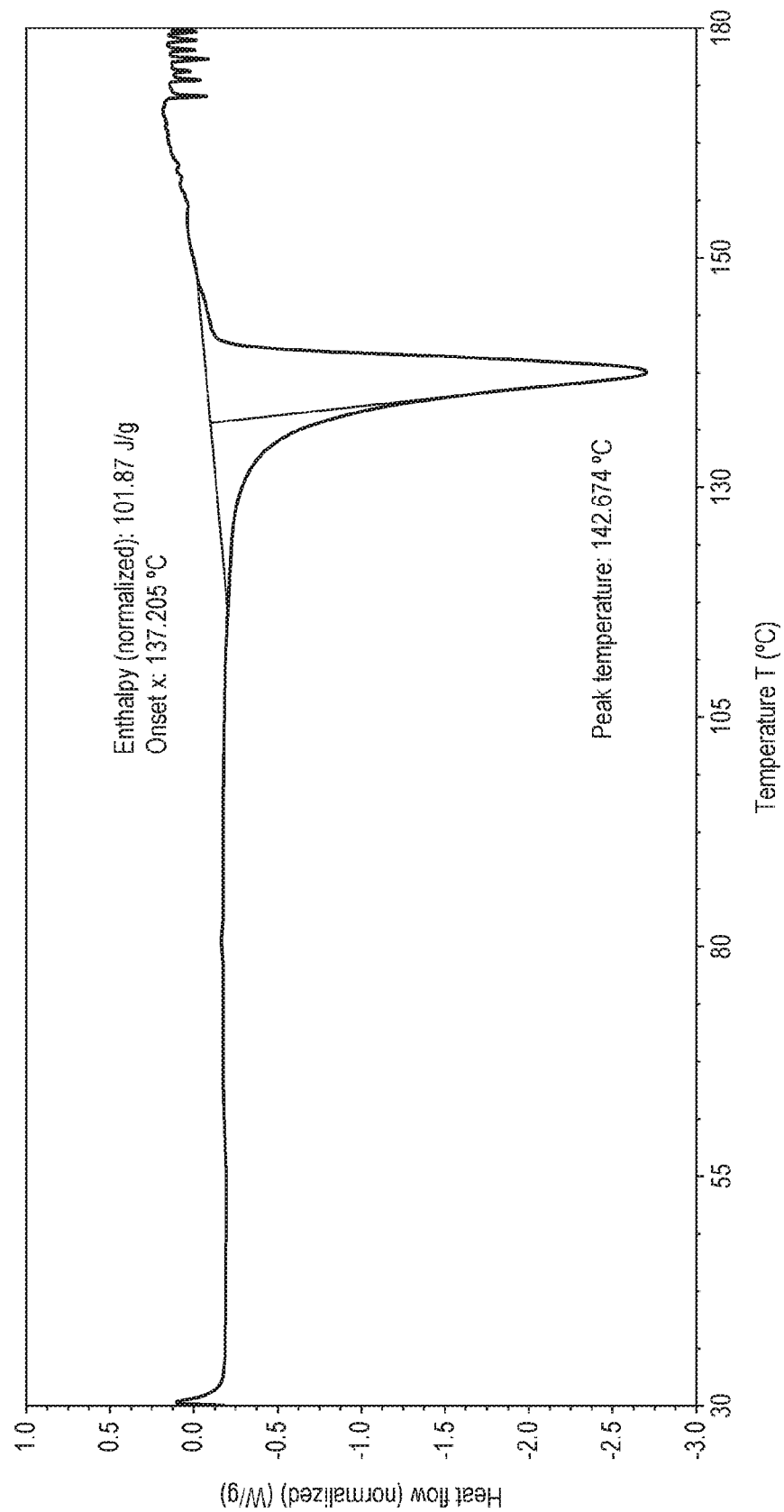
FIG. 9 differential scanning calorimetry (DSC) graph for Form III of the succinate salt of (((1-(6-amino-9H-purin-9-yl)propan-2-yloxy)methyl) (phenoxy) phosphoryloxy) methyl pivalate.

In one aspect, crystalline Form III may exhibit a differential scanning calorimetry (DSC) thermogram substantially as shown in FIG. 9

Those skilled in the art would recognize that Form III may be further characterized by other known analytical and/or spectroscopic methods including, but not limited to thermogravimetric analysis (TGA), dynamic vapor sorption (DVS), solid state NMR and Raman spectroscopy.

In another aspect, the pharmaceutically acceptable acid addition salt of the (((1-(6-amino-9H-purin-9-yl)propan-2-yloxy) methyl) (phenoxy) phosphoryloxy) methyl pivalate of Formula (I) is citric acid salt of formula (Id).

Formula I. Citric acid

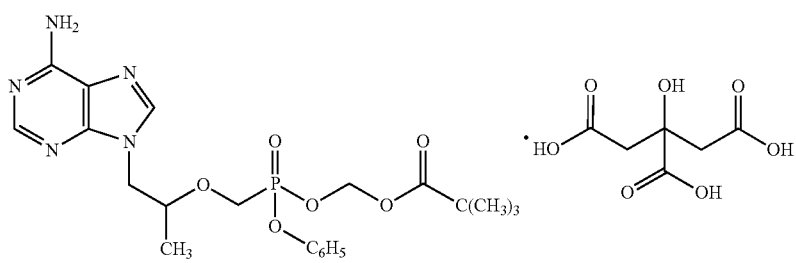

The citrate salt according to the present invention is a 1:1 salt of citric acid with (((1-(6-amino-9H-purin-9-yl)propan-2-yloxy) methyl) (phenoxy) phosphoryloxy) methyl pivalate. Thus citrate salt is monocitrate salt of formula (Id).

In a further aspect, the present invention relates to a process for preparing (((1-(6-amino-9H-purin-9-yl)propan-2-yloxy) methyl) (phenoxy) phosphoryloxy) methyl pivalate citric acid salt of formula (Id), which comprises reacting the free base of a (((1-(6-amino-9H-purin-9-yl)propan-2-yloxy) methyl) (phenoxy) phosphoryloxy) methyl pivalate of Formula (I) with citric acid.

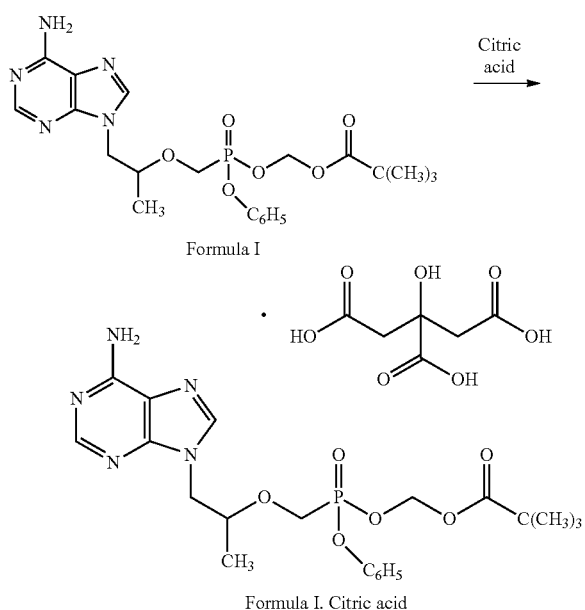

Formula I

Formula I. Citric acid

The citrate according to the invention is characterised by good crystallinity and low amorphisation during grinding and compression. In addition, it is not hygroscopic and is readily soluble in physiologically acceptable solvents.

In another aspect, the present invention provides crystalline polymorphic form of (((1-(6-amino-9H-purin-9-yl)propan-2-yloxy) methyl) (phenoxy) phosphoryloxy) methyl pivalate citric acid salt of formula (Id), hereinafter referred to as Form IV.

In one aspect, the crystalline Form IV is characterized by an X-ray powder diffraction pattern comprising the following 2θ values measured on a Rigaku, MiniFlex 2, tabletop X-ray powder diffractometer using CuKα, radiation.

Form IV may be characterized by having an XRD pattern comprising peaks at 5.48, 11.15, 15.4, 16.22, 22.57, and 25.68°2θ±0.2°2θ. The XRD pattern may comprise further peaks at 7.63, 14.45, 20.10, 20.55, and 21.01°2θ±0.2°2θ. The XRD pattern comprise still further peaks at 12.01, 16.77, 17.50, 18.67, 21.62, 25.21, and 28.52°2θ±0.2°2θ.

Figure 10:
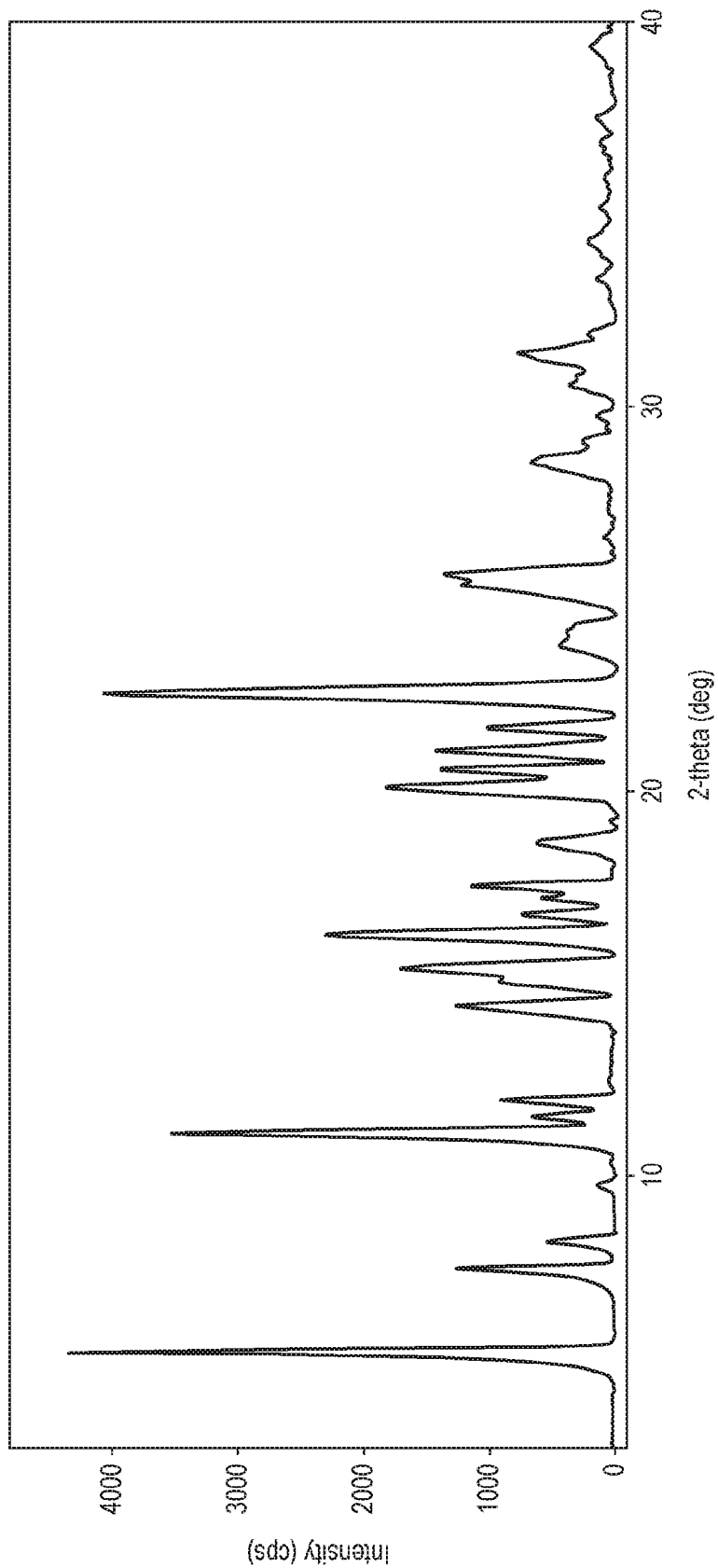
FIG. 10 shows the x-ray powder diffraction patterns (XRDs) for Form IV of the citrate salt of (((1-(6-amino-9H-purin-9-yl)propan-2-yloxy)methyl) (phenoxy) phosphoryloxy) methyl pivalate.

In one aspect, Form IV has an XRD pattern substantially as shown in FIG. 10.

In another aspect, Form IV has an XRD pattern with peaks at 2θ-values as shown in Table 4.

TABLE 4

| Diffraction angle (2θ-values) | Intensity (%) |
| --- | --- |
| 5.48 | 70.22 |
| 7.63 | 23.87 |
| 11.15 | 70.20 |
| 12.01 | 132.43 |
| 14.45 | 24.28 |
| 15.4 | 59.63 |
| 16.22 | 52.79 |
| 16.77 | 11.88 |
| 17.50 | 19.20 |
| 18.67 | 15.37 |
| 20.10 | 43.86 |
| 20.55 | 23.07 |
| 21.01 | 26.68 |
| 21.62 | 16.67 |
| 22.57 | 100.0 |
| 25.21 | 19.41 |

TABLE 4-continued

| Diffraction angle (2θ-values) | Intensity (%) |
| --- | --- |
| 25.68 | 61.92 |
| 28.52 | 16.48 |

Crystalline Form IV, may also be characterized by having an IR spectrum comprising characteristic IR spectra peaks at about 2977 $cm^{-1}$, 1741 $cm^{-1}$, 1679 $cm^{-1}$, 1663 $cm^{-1}$, 1622 $cm^{-1}$, 1590 $cm^{-1}$, 1488 $cm^{-1}$, 1458 $cm^{-1}$, 1421 $cm^{-1}$, 1396 $cm^{-1}$, 1252 $cm^{-1}$, 1197 $cm^{-1}$, 1127 $cm^{-1}$, 1023 $cm^{-1}$, 985 $cm^{-1}$, 823 $cm^{-1}$, 793 $cm^{-1}$, 720 $cm^{-1}$, and 688 $cm^{-1}$±2 $cm^{-1}$.

Figure 11:
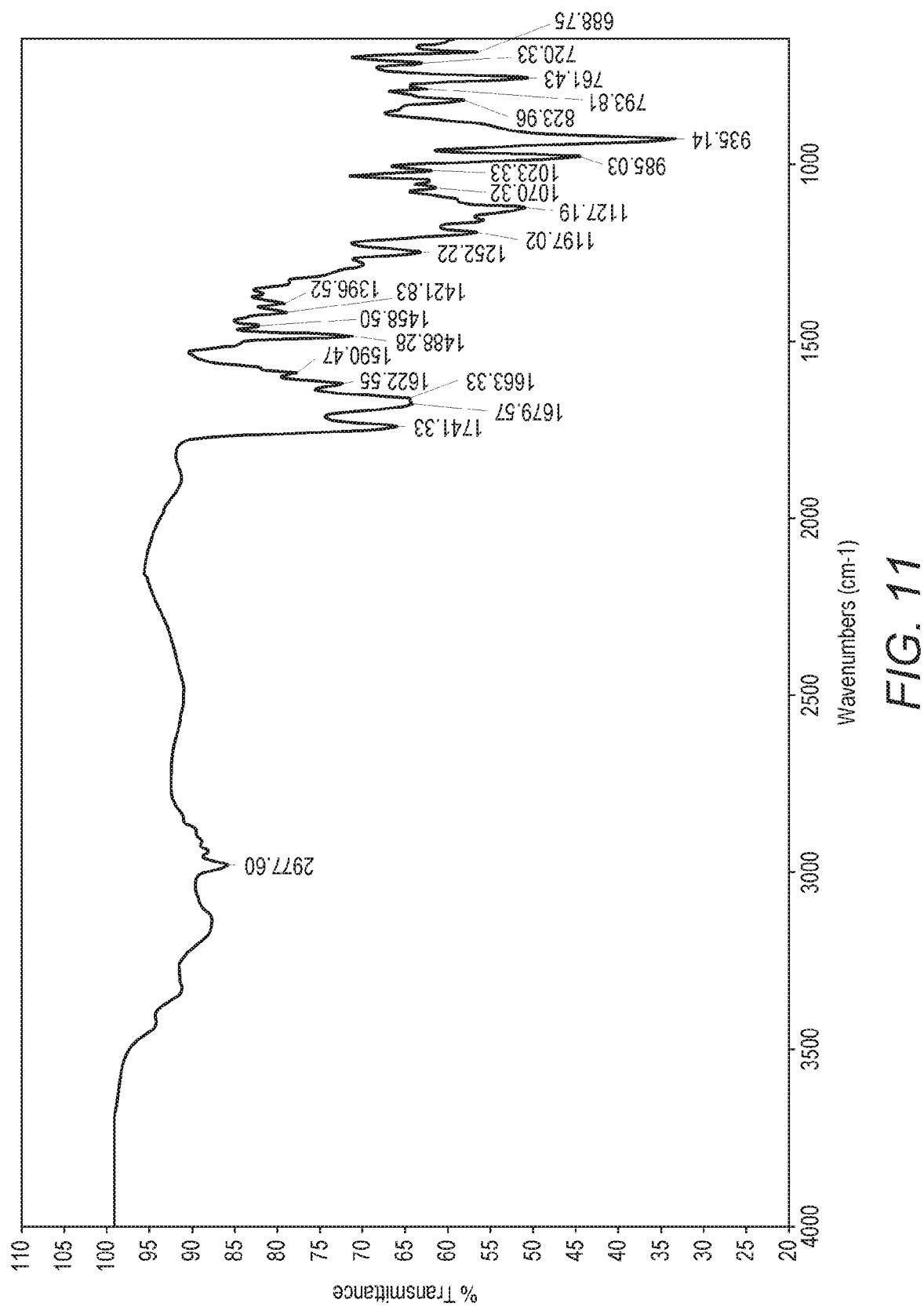
FIG. 11 shows an Infra-Red (IR) absorption spectrum for Form IV of the citrate salt of (((1-(6-amino-9H-purin-9-yl) propan-2-yloxy)methyl) (phenoxy) phosphoryloxy) methyl pivalate.

In one aspect, Form IV may exhibit an IR spectrum pattern substantially as shown in FIG. 11.

Form IV may also be characterized as having a DSC spectrum exhibiting a (exothermic) significant peak between about 102° C. and 108° C., preferably exhibiting a peak at about 102.9° C.

Figure 12:
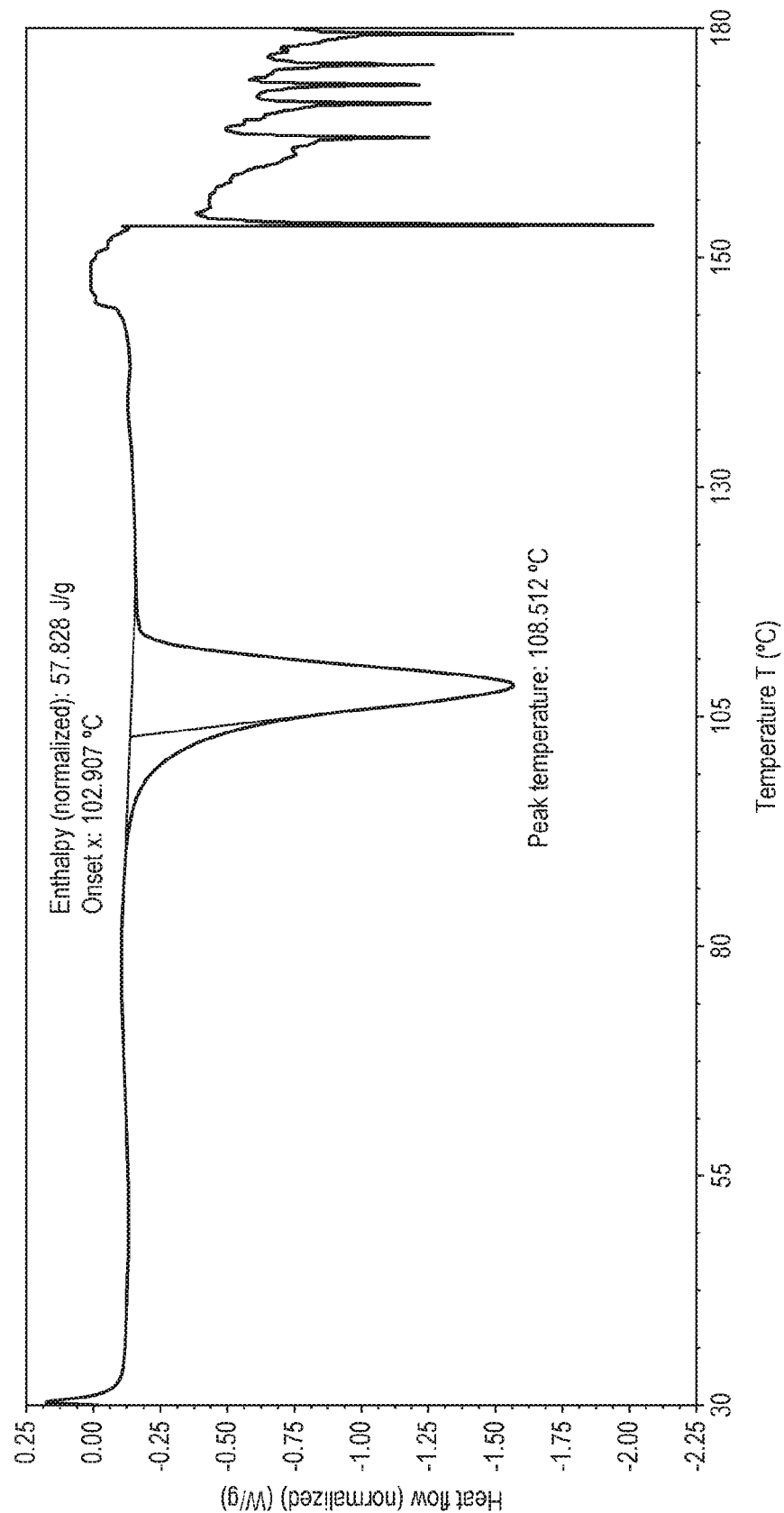
FIG. 12 differential scanning calorimetry (DSC) graph for Form IV of the citrate salt of (((1-(6-amino-9H-purin-9-yl) propan-2-yloxy)methyl) (phenoxy) phosphoryloxy) methyl pivalate

In another aspect, crystalline Form IV may exhibit a differential scanning calorimetry (DSC) thermogram substantially as shown in FIG. 12

Those skilled in the art would recognize that Form IV may be further characterized by other known analytical and/or spectroscopic methods including, but not limited to thermogravimetric analysis (TGA), dynamic vapor sorption (DVS), solid state NMR and Raman spectroscopy.

In another aspect, the present invention provides crystalline polymorphic form of (((1-(6-amino-9H-purin-9-yl)propan-2-yloxy) methyl) (phenoxy) phosphoryloxy) methyl pivalate tartaric acid salt of formula (Ie), hereinafter referred to as Form V.

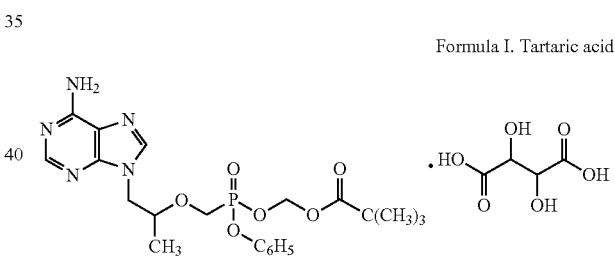

Formula I. Tartaric acid

In another aspect, the crystalline Form V is characterized by an X-ray powder diffraction pattern comprising the following 2θ values measured on a Rigaku, MiniFlex 2, tabletop X-ray powder diffractometer using CuKα, radiation.

In one aspect, the crystalline Form V is characterized by having an XRD pattern comprising peaks at 4.73, and 20.65°2θ±0.2°2θ. The XRD pattern may comprise further peaks at 16.47, 24.33, 25.07 and 29.26°2θ±0.2°2θ.

Figure 13:
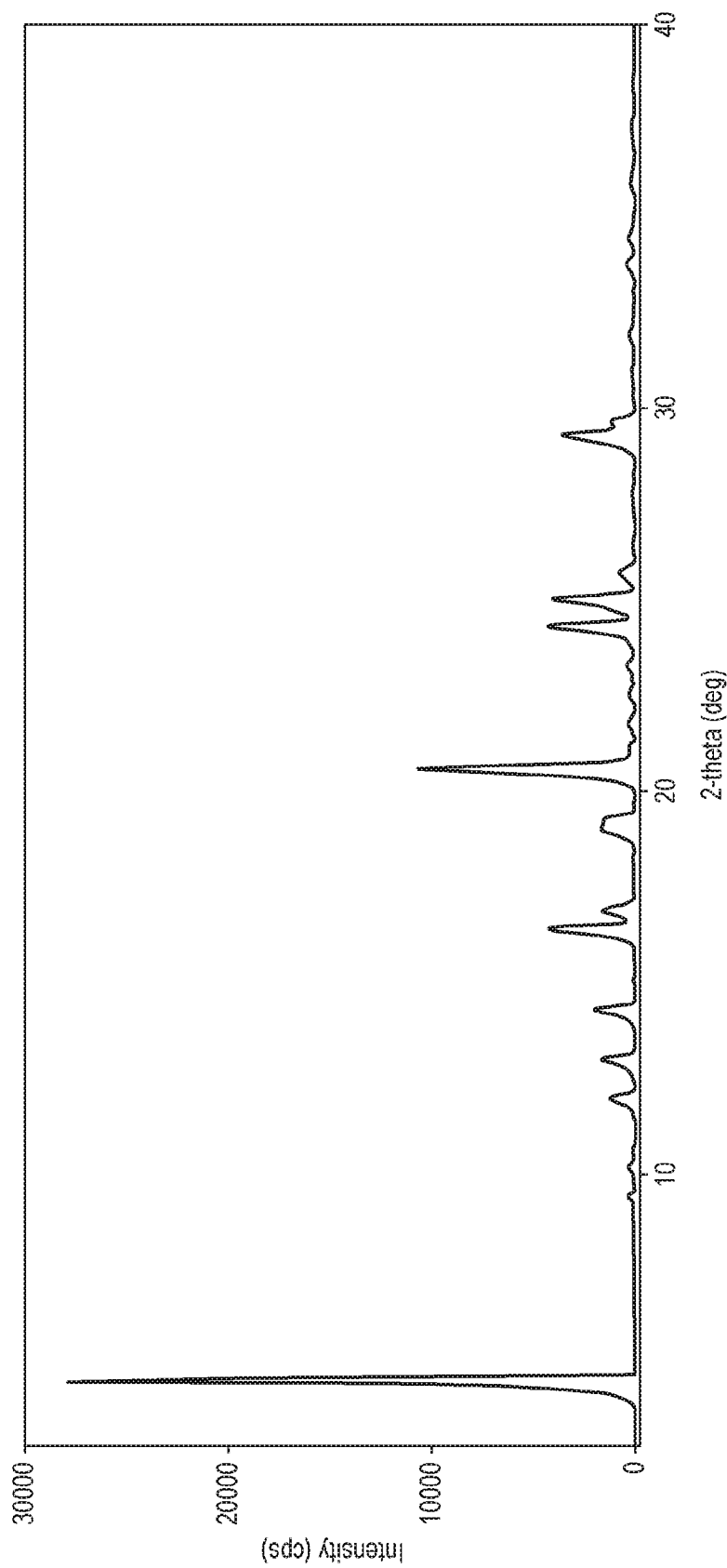
FIG. 13 shows the x-ray powder diffraction patterns (XRDs) for Form V of the tartrate salt of (((1-(6-amino-9H-purin-9-yl)propan-2-yloxy)methyl) (phenoxy) phosphoryloxy) methyl pivalate.

The Form V exhibits an X-ray powder diffraction (XRD) pattern substantially as shown in FIG. 13.

The crystalline polymorph Form V may have an XRD pattern with peaks at 2θ-values as shown in Table 5.

TABLE 5

| Diffraction angle (2θ-values) | Intensity (%) |
| --- | --- |
| 4.73 | 100.0 |
| 16.47 | 20.39 |
| 20.65 | 55.90 |

TABLE 5-continued

| Diffraction angle (2θ-values) | Intensity (%) |
|---|---|
| 24.33 | 20.10 |
| 25.07 | 22.85 |
| 29.26 | 28.48 |

Crystalline Form V may also be characterized by having an IR spectrum comprising characteristic IR spectra peaks at about 3315 cm$^{-1}$, 2975 cm$^{-1}$, 1745 cm$^{-1}$, 1726 cm$^{-1}$, 1679 cm$^{-1}$, 1624 cm$^{-1}$, 1591 cm$^{-1}$ 1489 cm$^{-1}$, 1420 cm$^{-1}$, 1389 cm$^{-1}$, 1324 cm$^{-1}$, 1273 cm$^{-1}$, 1199 cm$^{-1}$, 1141 cm$^{-1}$, 1104 cm$^{-1}$, 1068 cm$^{-1}$, 1025 cm$^{-1}$, 984 cm$^{-1}$, 831 cm$^{-1}$, 806 cm$^{-1}$, 764 cm$^{-1}$, 715 cm$^{-1}$, and 681 cm$^{-1}$±2 cm$^{-1}$.

Figure 14:
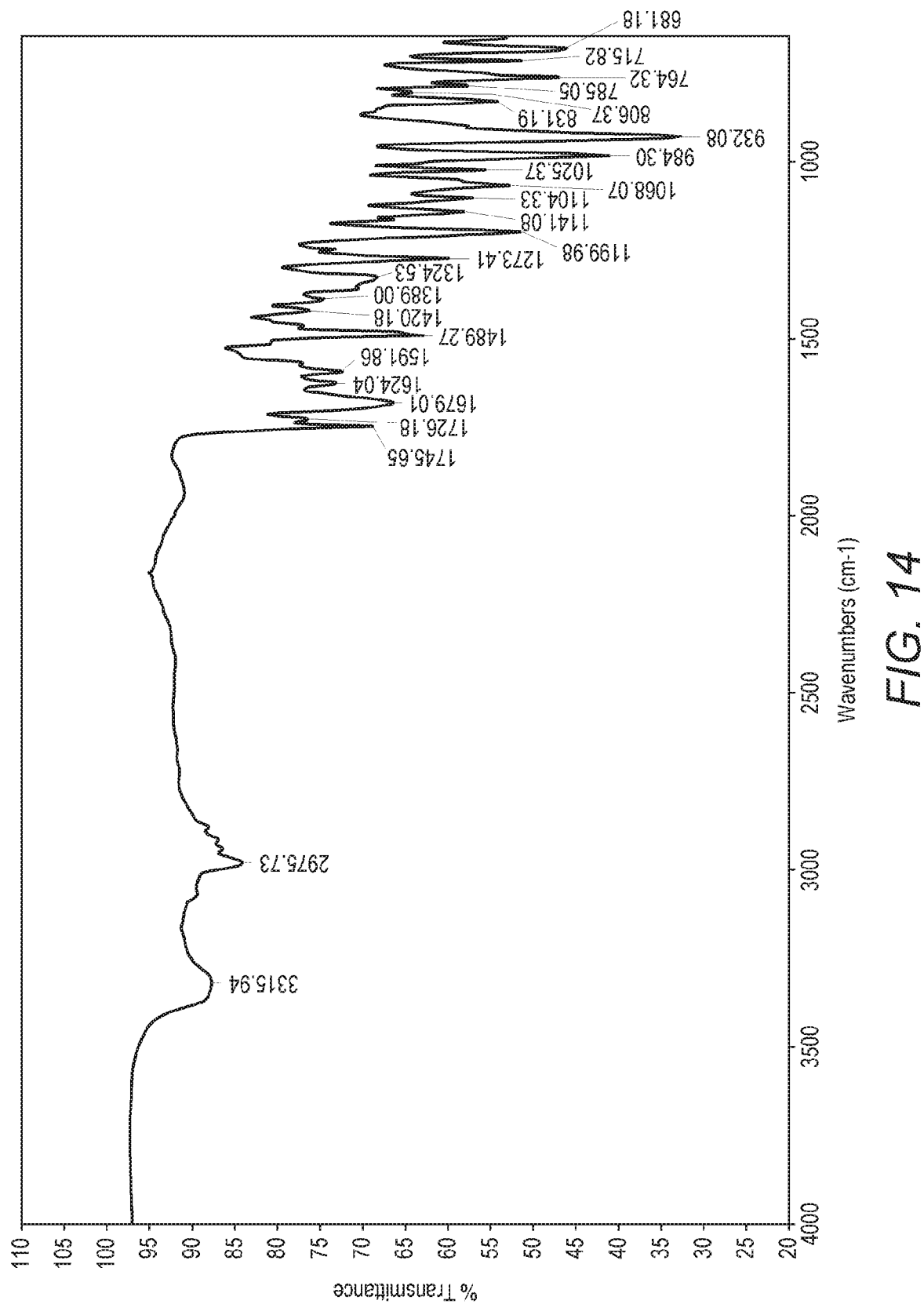
FIG. 14 shows an Infra-Red (IR) absorption spectrum for Form V of the tartrate salt of (((1-(6-amino-9H-purin-9-yl) propan-2-yloxy)methyl) (phenoxy) phosphoryloxy) methyl pivalate.

In one aspect, Form V may exhibit an IR spectrum pattern substantially as shown in FIG. 14.

Form V may also be characterized as having a DSC spectrum exhibiting a (exothermic) significant peak between about 137° C. and about 143° C., preferably exhibiting a peak at about 137.2° C.

Figure 15:
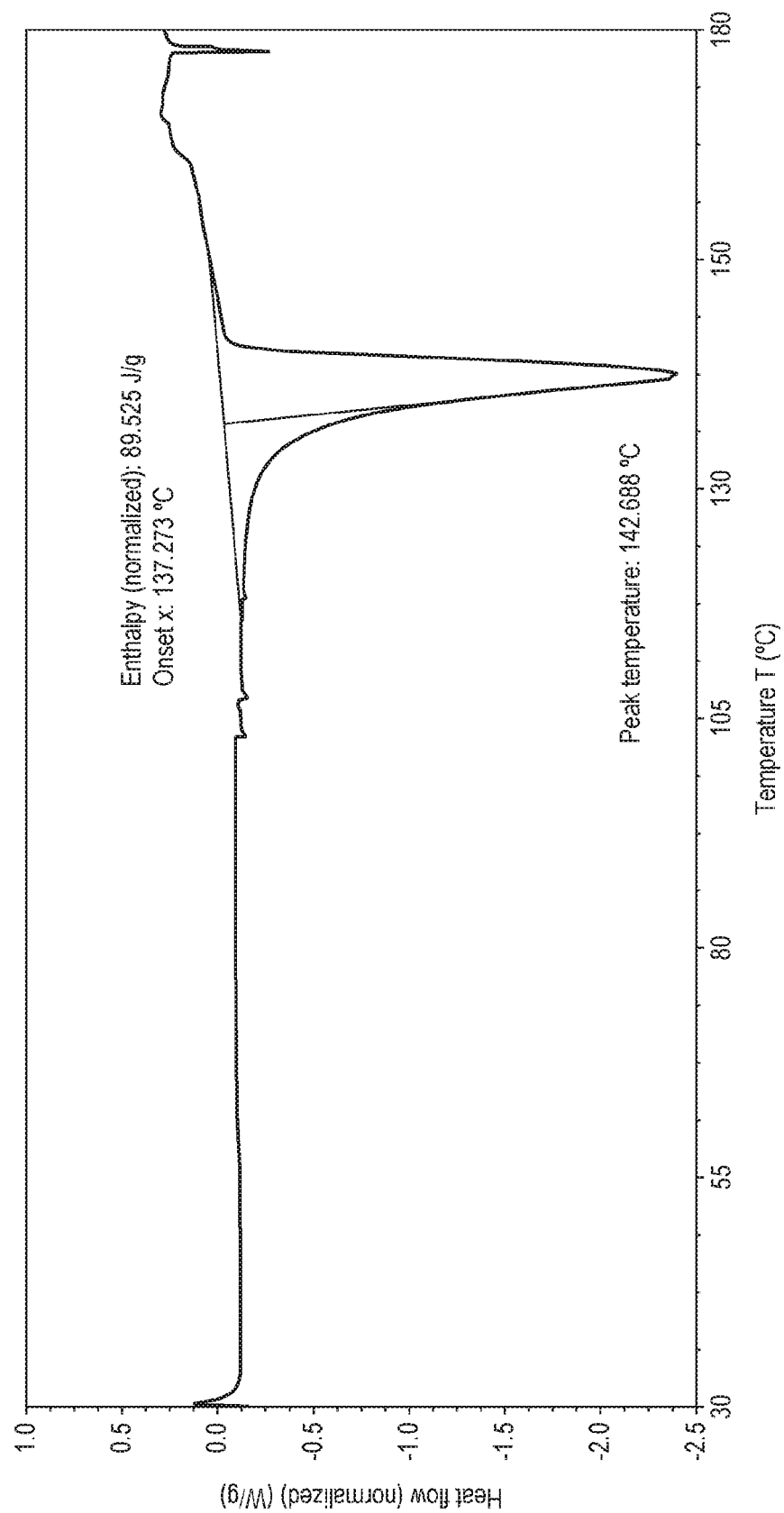
FIG. 15 differential scanning calorimetry (DSC) graph for Form V of the tartrate salt of (((1-(6-amino-9H-purin-9-yl) propan-2-yloxy)methyl) (phenoxy) phosphoryloxy) methyl pivalate.

In another aspect, Form V may exhibit a differential scanning calorimetry (DSC) thermogram substantially as shown in FIG. 15.

Those skilled in the art would recognize that Form V may be further characterized by other known analytical and/or spectroscopic methods including, but not limited to thermogravimetric analysis (TGA), dynamic vapor sorption (DVS), solid state NMR and Raman spectroscopy.

In a further aspect, the present invention relates to a process for preparing crystalline Form V of (((1-(6-amino-9H-purin-9-yl)propan-2-yloxy) methyl) (phenoxy) phosphoryloxy) methyl pivalate tartaric acid salt of formula (Ie), which comprises reacting the free base of a (((1-(6-amino-9H-purin-9-yl)propan-2-yloxy) methyl) (phenoxy) phosphoryloxy) methyl pivalate of Formula (I) with tartaric acid.

In another aspect, the present invention provides crystalline polymorphic form of (((1-(6-amino-9H-purin-9-yl)propan-2-yloxy) methyl) (phenoxy) phosphoryloxy) methyl pivalate fumaric acid salt of formula (If), hereinafter referred to as Form VI.

In one aspect, the crystalline Form VI is characterized by an X-ray powder diffraction pattern comprising the following 2θ values measured on a Rigaku, MiniFlex 2, tabletop X-ray powder diffractometer using CuKα, radiation.

In another aspect, Form VI is characterized by having an XRD pattern comprising peaks at 5.03, 23.59 and 29.02°2θ±0.2°2θ. The XRD pattern may comprise further peaks at 20.80, 21.2 and 26.04°2θ±0.2°2θ. The XRD pattern comprise still further peaks at 11.26, 12.89, 17.42 and 20.02°2θ±0.2°2θ.

Figure 16:
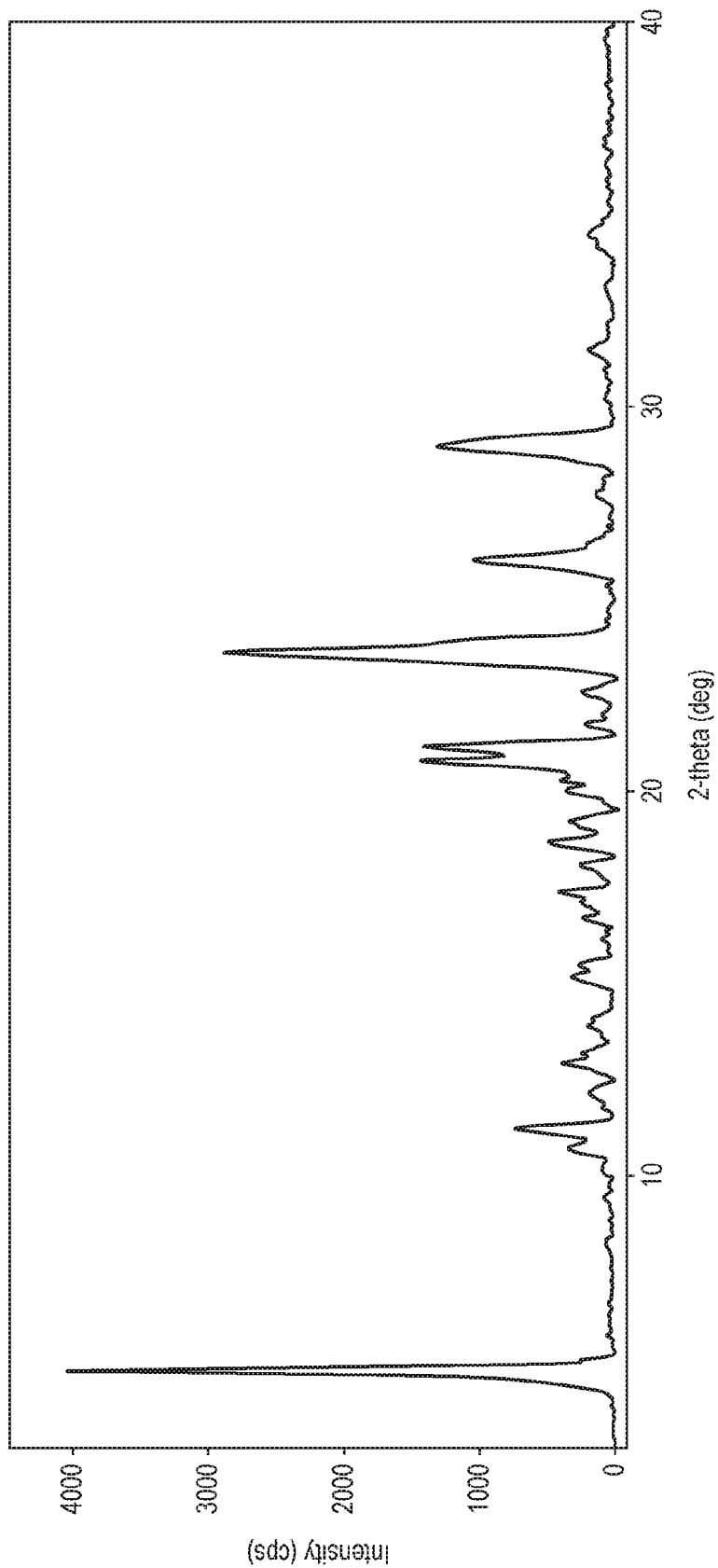
FIG. 16 shows the x-ray powder diffraction patterns (XRDs) for Form VI of the fumarate salt of (((1-(6-amino-9H-purin-9-yl)propan-2-yloxy)methyl) (phenoxy) phosphoryloxy) methyl pivalate.

In one aspect, Form VI has an XRD pattern substantially as shown in FIG. 16.

In one aspect, Form VI has an XRD pattern with peaks at 2θ-values as shown in Table 6.

TABLE 6

| Diffraction angle (2θ-values) | Intensity (%) |
|---|---|
| 5.03 | 72.78 |
| 11.26 | 18.00 |
| 12.89 | 10.52 |
| 17.42 | 12.14 |
| 20.02 | 13.44 |
| 20.80 | 21.50 |

TABLE 6-continued

| Diffraction angle (2θ-values) | Intensity (%) |
|---|---|
| 21.20 | 28.14 |
| 23.59 | 100.0 |
| 26.04 | 34.30 |
| 29.02 | 31.13 |

Form VI may also be characterized by having an IR spectrum comprising characteristic IR spectra peaks at about 3182 cm$^{-1}$, 3049 cm$^{-1}$, 2976 cm$^{-1}$, 1751 cm$^{-1}$, 1618 cm$^{-1}$, 1489 cm$^{-1}$, 1458 cm$^{-1}$, 1419 cm$^{-1}$, 1395 cm$^{-1}$, 1277 cm$^{-1}$, 1184 cm$^{-1}$, 1098 cm$^{-1}$, 1068 cm$^{-1}$, 980 cm$^{-1}$, 931 cm$^{-1}$, 830 cm$^{-1}$, 787 cm$^{-1}$, 762 cm$^{-1}$, 723 cm$^{-1}$, and 687 cm$^{-1}$±2 cm$^{-1}$.

Figure 17:
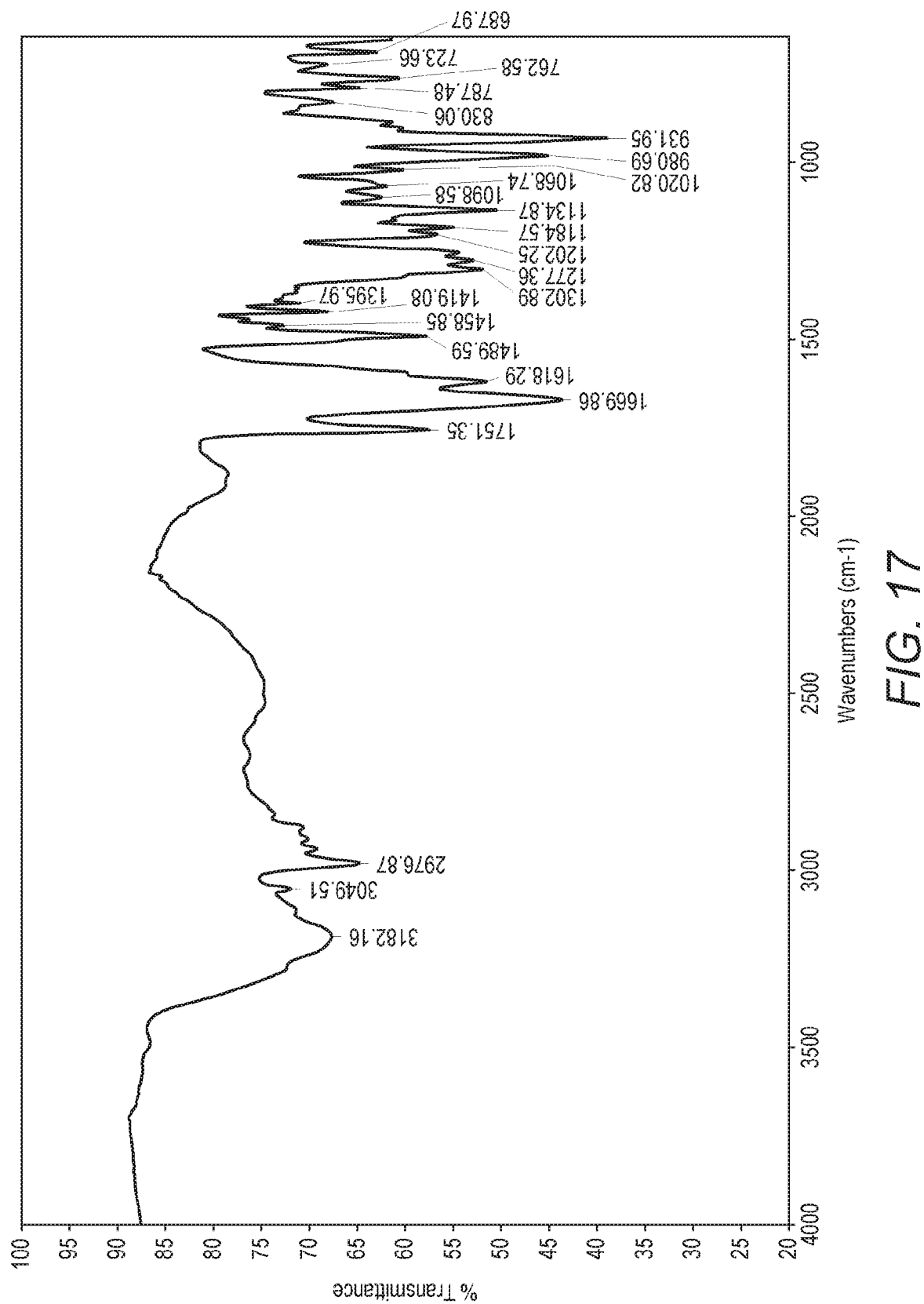
FIG. 17 shows an Infra-Red (IR) absorption spectrum for Form VI of the fumarate salt of (((1-(6-amino-9H-purin-9-yl)propan-2-yloxy)methyl) (phenoxy) phosphoryloxy) methyl pivalate.

In another aspect, Form VI may exhibit an IR spectrum pattern substantially as shown in FIG. 17.

Form VI may also be characterized as having a DSC spectrum exhibiting a (exothermic) significant peak between about 119.8° C. and about 123° C., preferably exhibiting a peak at about 119.8° C.

Figure 18:
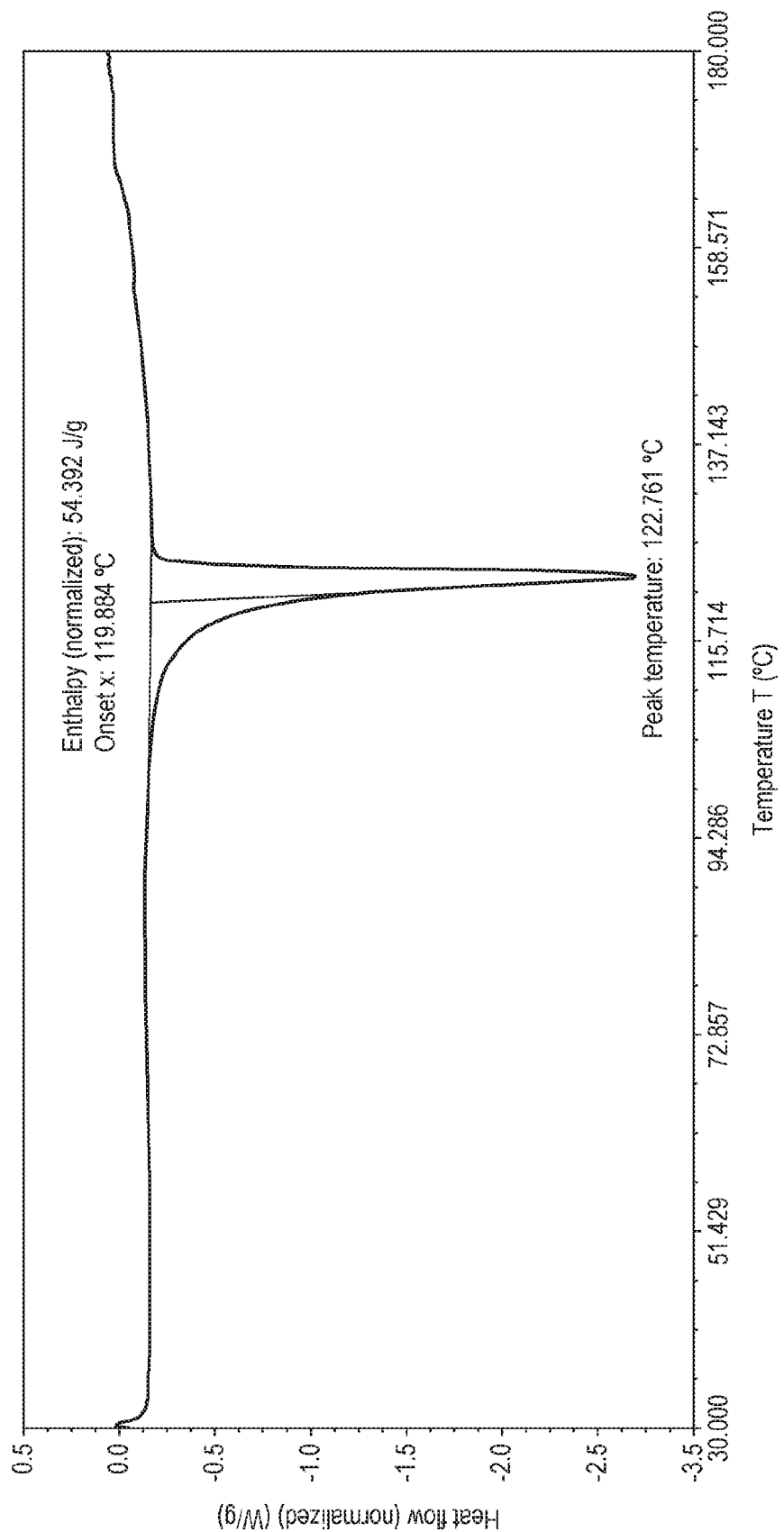
FIG. 18 differential scanning calorimetry (DSC) graph for Form VI of the fumarate salt of (((1-(6-amino-9H-purin-9-yl)propan-2-yloxy)methyl) (phenoxy) phosphoryloxy) methyl pivalate.

In another aspect, crystalline Form VI may exhibit a differential scanning calorimetry (DSC) thermogram substantially as shown in FIG. 18.

Those skilled in the art would recognize that Form VI may be further characterized by other known analytical and/or spectroscopic methods including, but not limited to thermogravimetric analysis (TGA), dynamic vapor sorption (DVS), solid state NMR and Raman spectroscopy.

In a further aspect, the present invention relates to a process for preparing crystalline Form VI of (((1-(6-amino-9H-purin-9-yl)propan-2-yloxy) methyl) (phenoxy) phosphoryloxy) methyl pivalate tartaric acid salt of formula (Ie), which comprises reacting the free base of a (((1-(6-amino-9H-purin-9-yl)propan-2-yloxy) methyl) (phenoxy) phosphoryloxy) methyl pivalate of Formula (I) with fumaric acid.

In one aspect, (((1-(6-amino-9H-purin-9-yl)propan-2-yloxy) methyl) (phenoxy) phosphoryloxy) methyl pivalate of Formula (I) is prepared by reacting compound 9-[2-(Phosphonomethoxy)propyl]adenine of Formula (II) with chloromethyl pivalate of Formula (III) in the presence of an auxiliary base. The auxiliary base can be an inorganic or organic base, and is preferably an organic base. In one aspect, the auxiliary bases are preferably tertiary amines, in particular trialkylamines. The reaction is suitably carried out in the presence of a solvent selected from polar aprotic solvent or mixtures thereof.

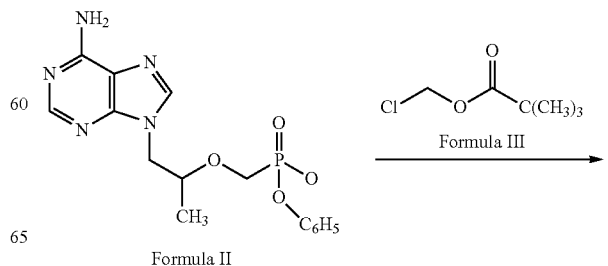

Formula II

Formula III

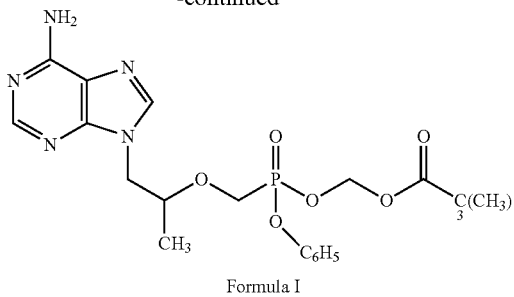

Formula I

The compound (((1-(6-amino-9H-purin-9-yl)propan-2-yloxy) methyl) (phenoxy) phosphoryloxy) methyl pivalate of Formula (I) may be converted to an acid addition salt either by first isolating the free base or without isolating the free base. In one aspect, (((1-(6-amino-9H-purin-9-yl)propan-2-yloxy) methyl) (phenoxy) phosphoryloxy) methyl pivalate of Formula (I) is not isolated, i.e. the free base is converted to an acid salt in situ.

In one aspect, (((1-(6-amino-9H-purin-9-yl)propan-2-yloxy) methyl) (phenoxy) phosphoryloxy) methyl pivalate of Formula (I) is dissolved in a suitable solvent to facilitate formation of the acid salt. Suitable solvents include, but are not limited to, polar solvents and mixtures thereof. Examples of suitable solvents include, but are not limited to, alcohols such as methanol, ethanol, isopropanol, butanol, 1,2-dimethoxy ethanol, 2-methoxy ethanol, 2-ethoxy ethanol and ethylene glycol, and like or mixtures thereof; ethers such as tetrahydrofuran, diethyl ether, 1,4-dioxane, DIPE, MTBE, and like; ketones such as acetone, MIBK; aprotic polar solvents such as DMF, dimethyl acetamide, dimethyl sulfoxide or mixtures thereof; esters like ethyl acetate and isopropyl acetate; chlorinated solvents like chloroform, dichloromethane, nitriles like acetonitrile, hydrocarbons such as benzene, toluene, xylene and the like or mixtures thereof. Preferably, the solvent is one or more solvents selected from the group consisting of aprotic solvents, hydrocarbons, ethers, alcohols and ketones. More preferably, the solvent is selected from isopropyl alcohol (IPA), methanol and acetone, or any combination thereof.

The solution containing (((1-(6-amino-9H-purin-9-yl) propan-2-yloxy) methyl) (phenoxy) phosphoryloxy) methyl pivalate of Formula (I) is treated with phosphoric acid, oxalic acid, succinic acid salt, citric acid, fumaric acid or tartaric acid. The acid may be in the form of a solution or solid. The resulting acid addition salt may be isolated as a solid by any known technique, including but not limited to, cooling, chilling, completely or partially distilling solvents, and/or filtering.

Alternatively, acid addition salts of (((1-(6-amino-9H-purin-9-yl)propan-2-yloxy) methyl) (phenoxy) phosphoryloxy) methyl pivalate of Formula (I) may be prepared in accordance with the present invention by a salt interconversion method. This process involves reacting an acid salt of (((1-(6-amino-9H-purin-9-yl)propan-2-yloxy) methyl) (phenoxy) phosphoryloxy) methyl pivalate with a suitable base to form the free base of (((1-(6-amino-9H-purin-9-yl)propan-2-yloxy) methyl) (phenoxy) phosphoryloxy) methyl pivalate of Formula (I) and thereafter converting the free base so formed into an acid salt form (by addition of an acid).

In certain aspects, the acid salts and polymorphic forms described herein may potentially exhibit improved properties. For example, in certain aspects, the acid salts and polymorphic forms described herein may potentially exhibit improved stability. Such improved stability could have a potentially beneficial impact on the manufacture of the Compound of Formula (I), such as for example offering the ability to store process intermediate for extended periods of time. Improved stability could also potentially benefit a composition or pharmaceutical composition of the Compound of Formula (I). In further aspects, the salts and polymorphic forms described herein may also potentially result in improved yield of the Compound of Formula (I), or potentially result in an improvement of the quality of the Compound of Formula (I). In certain aspects, the salts and polymorphic described herein may also exhibit improved pharmacokinetic properties and/or potentially improved bioavailability.

The acid salts and polymorphic forms of the present invention may be administered by any route appropriate to the condition to be treated. Suitable administration routes include, but are not limited to, oral, rectal, nasal, pulmonary, topical, vaginal and parenteral.

The pharmaceutical compositions of the present invention comprise a compound of Formula (I) or a pharmaceutically acceptable acid addition salt thereof of the type disclosed herein, together with one or more pharmaceutically acceptable excipients, and optionally one or more further active pharmaceutical ingredients.

In one aspect, the pharmaceutical composition of the present invention is formulated to provide immediate release of the active pharmaceutical ingredient(s) present therein. In an alternative aspect, the pharmaceutical composition of the present invention is formulated to provide controlled release of the active pharmaceutical ingredient(s) present therein. Controlled release comprises delayed, sustained and pulsed release of the active pharmaceutical ingredient(s).

Suitable pharmaceutical excipients are known in the art and include, but are not limited to, carriers, diluents and/or vehicles. The excipients (s) must be "acceptable" in the sense of being compatible with the other ingredients of the pharmaceutical composition and not harmful to the patient. The excipient(s) may be selected to provide a desired release profile of the active pharmaceutical ingredient(s) present.

The pharmaceutical compositions of the present invention comprise a therapeutically effective amount of a compound of Formula (I) or a pharmaceutically acceptable acid addition salt thereof. Suitable dosages include, but are not limited to, 25 mg, 50 mg, 100 mg, 150 mg, 200 mg, 250 mg and 300 mg.

In one aspect of the present invention there is provided an acid salt of (((1-(6-amino-9H-purin-9-yl)propan-2-yloxy) methyl) (phenoxy) phosphoryloxy) methyl pivalate having an intrinsic dissolution profile as shown in FIG. 20.

In one aspect of the present invention there is provided an acid salt of (((1-(6-amino-9H-purin-9-yl)propan-2-yloxy) methyl) (phenoxy) phosphoryloxy) methyl pivalate having an intrinsic dissolution profile as shown in Table 8.

In one aspect of the present invention the (((1-(6-amino-9H-purin-9-yl)propan-2-yloxy) methyl) (phenoxy) phosphoryloxy) methyl pivalate fumaric acid salt exhibits a dissolution of at least about 10% at about 30 minutes and/or about 20% at about 60 minutes and/or about 40% at about 120 minutes and/or about 60% at about 180 minutes and/or about 80% at about 240 minutes.

In a further aspect of the present invention the (((1-(6-amino-9H-purin-9-yl)propan-2-yloxy) methyl) (phenoxy) phosphoryloxy) methyl pivalate oxalic acid salt exhibits a dissolution of at least about 5% at about 30 minutes and/or about 10% at about 60 minutes and/or about 30% at about 120 minutes and/or about 40% at about 180 minutes and/or about 60% at about 240 minutes.

In a further aspect of the present invention the (((1-(6-amino-9H-purin-9-yl)propan-2-yloxy) methyl) (phenoxy) phosphoryloxy) methyl pivalate phosphoric acid salt exhibits a dissolution of at least about 90% (preferably about 100%) at about 30 minutes.

In a further aspect of the present invention the (((1-(6-amino-9H-purin-9-yl)propan-2-yloxy) methyl) (phenoxy) phosphoryloxy) methyl pivalate citric acid salt exhibits a dissolution of at least about 20% at about 30 minutes and/or about 40% at about 60 minutes and/or about 70% at about 120 minutes.

In a further aspect of the present invention the (((1-(6-amino-9H-purin-9-yl)propan-2-yloxy) methyl) (phenoxy) phosphoryloxy) methyl pivalate succinic acid salt exhibits a dissolution of at least about 10% at 30 minutes and/or about 30% at about 60 minutes and/or about 80% at about 180 minutes and/or about 90% at about 240 minutes.

In a further aspect of the present invention the (((1-(6-amino-9H-purin-9-yl)propan-2-yloxy) methyl) (phenoxy) phosphoryloxy) methyl pivalate tartaric acid salt exhibits a dissolution of at least about 10% release at about 30 minutes and/or about 20% release at about 60 minutes and/or about 40% at 120 minutes and/or about 70% at about 180 minutes and/or about 80% at about 240 minutes.

The following examples, which include preferred aspects, will serve to illustrate the practice of this invention, it being understood that the particulars shown are by way of example and for purpose of illustrative discussion of preferred aspects of the invention.

EXAMPLES

XRD

Powder X-ray diffraction patterns were measured using a commercially available Rigaku, Minflex 2, tabletop diffractometer using a copper-K-α radiation source. Measurements of 2θ values are accurate to within ±0.2 degrees.

DSC

Differential scanning calorimetry (DSC) data was obtained using the following commercially available apparatus and experimental conditions:

Instrument Make and Model: TA Waters and Discovery DSC

Temperature Range: 30 to 200° C.

Heating Rate: 10° C. per min $N_2$ Flow: 50 ml

Pan Type: Tzero Sealed Pan

IR

IR spectra were recorded on a commercially available Bruker Alpha IR spectrometer. Samples were prepared by known methods using a KBr dispersion (sample concentration 1%).

Example-1 Preparation of Phosphate Salt of (((1-(6-amino-9H-purin-9-yl)propan-2-yloxy)methyl) (phenoxy) phosphoryloxy) methyl pivalate 9-[2-(Phosphonomethoxy)propyl]adenine (100 gm, 0.275 mole) stirred in dimethyl carbonate (500 ml) at room temperature. Tetrabutyl ammonium bromide (30 gm, 0.093 mole) and N,N-Diisopropylethyl amine (53.3 gm, 0.41 mole) added to reaction mass at room temperature. Raised the temperature of the reaction mass to 60-65° C. Chloromethyl pivalate (62 gm, 0.41 mole) added to the reaction mass 60-65° C. The reaction mass further stirred at 60-65° C. for 5 hrs and the organic solvent distilled out under vacuum. The residue was dissolved in dichloromethane (500 ml) and washed with 10% sodium dihydrogen phosphate buffer solution (200 ml). Dichloromethane was distilled out completely and the residue was stirred in isopropyl alcohol (500 ml). Ortho phosphoric acid (32 gm, 0.32 mole) added to the reaction mass and the temperature of the reaction mass raised to 70-75° C. The reaction mass was cooled to the room temperature and the solid was isolated by filtration to obtain the phosphate salt in the crystallized form. Yield: 110 gm.

The crystalline phosphate salt of Form I was characterized by XRD, IR and DSC. (FIGS. 1-3)

Example-2 Preparation of Oxalate Salt of (((1-(6-amino-9H-purin-9-yl)propan-2-yloxy)methyl) (phenoxy) phosphoryloxy) methyl pivalate 9-[2-(Phosphonomethoxy)propyl]adenine (100 gm, 0.275 mole) stirred in dimethyl carbonate (500 ml) at room temperature. Tetrabutyl ammonium bromide (30 gm, 0.093 mole) and N,N-Diisopropylethyl amine (53.3 gm, 0.41 mole) added to reaction mass at room temperature. Raised the temperature of the reaction mass to 60-65° C. Chloromethyl pivalate (62 gm, 0.41 mole) added to the reaction mass 60-65° C. The reaction mass further stirred at 60-65° C. for 5 hrs and the organic solvent distilled out under vacuum. The residue was dissolved in dichloromethane (500 ml) and washed with 10% sodium dihydrogen phosphate buffer solution (200 ml). Dichloromethane was distilled out completely and the residue was stirred in methanol (500 ml). Oxalic acid (38 gm, 0.30 mole) added to the reaction mass and the temperature of the reaction mass raised to 55-60° C. The reaction mass was cooled to the room temperature and the solid was isolated by filtration to obtain the oxalate salt in the crystallized form. Yield: 115 gm.

The crystalline oxalate salt of Form II was characterized by XRD, IR and DSC. (FIGS. 4-6)

Example-3 Preparation of Succinate Salt of (((1-(6-amino-9H-purin-9-yl)propan-2-yloxy)methyl) (phenoxy) phosphoryloxy) methyl pivalate 9-[2-(Phosphonomethoxy)propyl]adenine (100 gm, 0.275 mole) stirred in dimethyl carbonate (500 ml) at room temperature. Tetrabutyl ammonium bromide (30 gm, 0.093 mole) and N,N-Diisopropylethyl amine (53.3 gm, 0.41 mole) added to reaction mass at room temperature. Raised the temperature of the reaction mass to 60-65° C. Chloromethyl pivalate (62 gm, 0.41 mole) added to the reaction mass 60-65° C. The reaction mass further stirred at 60-65° C. for 5 hrs and the organic solvent distilled out under vacuum. The residue was dissolved in dichloromethane (500 ml) and washed with 10% sodium dihydrogen phosphate buffer solution (200 ml). Dichloromethane was distilled out completely and the residue was stirred in acetone (500 ml). Succinic acid (33 gm, 0.27 mole) added to the reaction mass and the temperature of the reaction mass raised to 50-55° C. The reaction mass was cooled to the room temperature and the solid was isolated by filtration to obtain the succinate salt in the crystallized form. Yield: 95 gm.

The crystalline succinate salt of Form III was characterized by XRD, IR and DSC. (FIGS. 7-9)

Example 4 Preparation of Citrate of (((1-(6-amino-9H-purin-9-yl)propan-2-yloxy)methyl) (phenoxy) phosphoryloxy) methyl pivalate 9-[2-(Phosphonomethoxy)propyl]adenine (100 gm, 0.275 mole) stirred in dimethyl carbonate (500 ml) at room temperature. Tetrabutyl ammonium bromide (30 gm, 0.093 mole) and N,N-Diisopropylethyl amine (53.3 gm, 0.41 mole) added to reaction mass at room temperature. Raised the temperature of the reaction mass to 60-65° C. Chloromethyl pivalate (62 gm, 0.41 mole) added to the reaction mass 60-65° C. The reaction mass further stirred at 60-65° C. for 5 hrs and the organic solvent distilled out under vacuum. The residue was dissolved in dichloromethane (500 ml) and washed with 10% sodium dihydrogen phosphate buffer solution (200 ml). Dichloromethane was distilled out completely and the residue was stirred in acetone (500 ml). Citric acid (52 gm, 0.27 mole) added to the reaction mass and the temperature of the reaction mass raised to 50-55° C. The reaction mass was cooled to the room temperature and the solid was isolated by filtration to obtain the oxalate salt in the crystallized form. Yield: 115 gm.
The crystalline citrate salt of Form IV was characterized by XRD, IR and DSC. (FIGS. 10-12)

Example 5 Preparation of Tartrate Salt of (((1-(6-amino-9H-purin-9-yl)propan-2-yloxy)methyl) (phenoxy) phosphoryloxy) methyl pivalate 9-[2-(Phosphonomethoxy)propyl]adenine (100 gm, 0.275 mole) stirred in dimethyl carbonate (500 ml) at room temperature. Tetrabutyl ammonium bromide (30 gm, 0.093 mole) and N,N-Diisopropylethyl amine (53.3 gm, 0.41 mole) added to reaction mass at room temperature. Raised the temperature of the reaction mass to 60-65° C. Chloromethyl pivalate (62 gm, 0.41 mole) added to the reaction mass 60-65° C. The reaction mass further stirred at 60-65° C. for 5 hrs and the organic solvent distilled out under vacuum. The residue was dissolved in dichloromethane (500 ml) and washed with 10% sodium dihydrogen phosphate buffer solution (200 ml). Dichloromethane was distilled out completely and the residue was stirred in acetone (500 ml). L (+) Tartaric acid (41 gm, 0.27 mole) added to the reaction mass and the temperature of the reaction mass raised to 50-55° C. The reaction mass was cooled to the room temperature and the solid was isolated by filtration to obtain the oxalate salt in the crystallized form. Yield: 80 gm.
The crystalline tartrate salt of Form V was characterized by XRD, IR and DSC. (FIGS. 13-15)

Example 6 Preparation of Fumarate Salt of (((1-(6-amino-9H-purin-9-yl)propan-2-yloxy)methyl) (phenoxy) phosphoryloxy) methyl pivalate Phosphate salt of (((1-(6-amino-9H-purin-9-yl)propan-2-yloxy)methyl) (phenoxy) phosphoryloxy) methyl pivalate (100 gm, 0.17 mole) stirred in a mixture of dichloromethane (500 ml) and purified water (300 ml) at room temperature. Aq. Ammonia (100 ml) added to the reaction mass and stirred for 15 min at room temperature. The organic layer was separated and washed with 10% sodium dihydrogen phosphate buffer solution (200 ml). Dichloromethane was distilled out completely and the residue was stirred in isopropanol (500 ml). Fumaric acid (20 gm, 0.17 mole) added to the reaction mass and the temperature of the reaction mass raised to 70-75° C. The reaction mass was cooled to the room temperature and the solid was isolated by filtration to obtain the fumarate salt in the crystallized form. Yield: 80 gm.
The crystalline fumarate salt of Form VI was characterized by XRD, IR and DSC. (FIGS. 16-18)

Example 7 Preparation of tartrate Salt of (((1-(6-amino-9H-purin-9-yl)propan-2-yloxy)methyl) (phenoxy) phosphoryloxy) methyl pivalate Phosphate salt of (((1-(6-amino-9H-purin-9-yl)propan-2-yloxy)methyl) (phenoxy) phosphoryloxy) methyl pivalate (100 gm, 0.17 mole) stirred in a mixture of dichloromethane (500 ml) and purified water (300 ml) at room temperature. Aq. Ammonia (100 ml) added to the reaction mass and stirred for 15 min at room temperature. The organic layer was separated and washed with 10% sodium dihydrogen phosphate buffer solution (200 ml). Dichloromethane was distilled out completely and the residue was stirred in acetone (500 ml). Tartaric acid (26 gm, 0.17 mole) added to the reaction mass and the temperature of the reaction mass raised to 50-55° C. The reaction mass was cooled to the room temperature and the solid was isolated by filtration to obtain the tartrate salt in the crystallized form. Yield: 70 gm.
The crystalline tartrate salt of Form V was characterized by XRD, IR and DSC. (FIGS. 13-15)

Example 8 Preparation of Oxalate Salt of (((1-(6-amino-9H-purin-9-yl)propan-2-yloxy)methyl) (phenoxy) phosphoryloxy) methyl pivalate Phosphate salt of (((1-(6-amino-9H-purin-9-yl)propan-2-yloxy)methyl) (phenoxy) phosphoryloxy) methyl pivalate (100 gm, 0.17 mole) stirred in a mixture of dichloromethane (500 ml) and purified water (300 ml) at room temperature. Aq. Ammonia (100 ml) added to the reaction mass and stirred for 15 min at room temperature. The organic layer was separated and washed with 10% sodium dihydrogen phosphate buffer solution (200 ml). Dichloromethane was distilled out completely and the residue was stirred in methanol (500 ml). Oxalic acid (22 gm, 0.17 mole) added to the reaction mass and the temperature of the reaction mass raised to 50-55° C. The reaction mass was cooled to the room temperature and the solid was isolated by filtration to obtain the oxalate salt in the crystallized form. Yield: 80 gm.
The crystalline oxalate salt of Form II was characterized by XRD, IR and DSC. (FIGS. 4-6)

Example 9 Preparation of Citrate Salt of (((1-(6-amino-9H-purin-9-yl)propan-2-yloxy)methyl) (phenoxy) phosphoryloxy) methyl pivalate Phosphate salt of (((1-(6-amino-9H-purin-9-yl)propan-2-yloxy)methyl) (phenoxy) phosphoryloxy) methyl pivalate (100 gm, 0.17 mole) stirred in a mixture of dichloromethane (500 ml) and purified water (300 ml) at room temperature. Aq. Ammonia (100 ml) added to the reaction mass and stirred for 15 min at room temperature. The organic layer was separated and washed with 10% sodium dihydrogen phosphate buffer solution (200 ml). Dichloromethane was distilled out completely and the residue was stirred in acetone (500 ml). Citric acid (33 gm, 0.17 mole) added to the reaction mass and the temperature of the reaction mass raised to 50-55° C. The reaction mass was cooled to the room temperature and the solid was isolated by filtration to obtain the citrate salt in the crystallized form. Yield: 80 gm.
The crystalline citrate salt of Form IV was characterized by XRD, IR and DSC. (FIGS. 10-12)

Example 10 Preparation of Succinate Salt of (((1-(6-amino-9H-purin-9-yl)propan-2-yloxy)methyl) (phenoxy) phosphoryloxy) methyl pivalate Phosphate salt of (((1-(6-amino-9H-purin-9-yl)propan-2-yloxy)methyl) (phenoxy) phosphoryloxy) methyl pivalate (100 gm, 0.17 mole) stirred in a mixture of dichloromethane (500 ml) and purified water (300 ml) at room temperature. Aq. Ammonia (100 ml) added to the reaction mass and stirred for 15 min at room temperature. The organic layer was separated and washed with 10% sodium dihydrogen phosphate buffer solution (200 ml). Dichloromethane was distilled out completely and the residue was stirred in acetone (500 ml). Succinic acid (22 gm, 0.17 mole) added to the reaction mass and the temperature of the reaction mass raised to 50-55° C. The reaction mass was cooled to the room temperature and the solid was isolated by filtration to obtain the succinate salt in the crystallized form. Yield: 65 gm.

The crystalline succinate salt of Form III was characterized by XRD, IR and DSC. (FIGS. 7-9)

Example 11 Preparation of Tablet

General process for preparing tableting mixture comprising salt of (((1-(6-amino-9H-purin-9-yl)propan-2-yloxy) methyl) (phenoxy) phosphoryloxy) methyl pivalate.

A tableting mixture (200 mg) comprising solely salts of (((1-(6-amino-9H-purin-9-yl)propan-2-yloxy)methyl) (phenoxy) phosphoryloxy) methyl pivalate-prepared according to any one of the examples 1 to 10 (i.e. with no excipients) was prepared and compressed to a pellet using an automatic KBR press operating at a compression pressure of 2 tones for 2 minutes.

General Process for Preparing Tableting Mixture Comprising TAF:

Similarly a tableting mixture (200 mg) comprising a solely TAF (i.e. with no excipients) was prepared and compressed to a pellet using an automatic KBR press operating at a compression pressure of 2 tones for 2 minutes.

General Process for Preparing Tableting Mixture Comprising TDF:

A tableting mixture (200 mg) comprising solely TDF (i.e. with no excipients) was prepared and compressed to a pellet using an automatic KBR press operating at a compression pressure of 2 tones for 2 minutes.

In-vitro dissolution studies were performed on the 200 mg pellet in a LAB INDIA DISSO 2000.

The pellet was fixed in a PFTE holder, such that only the pellet surface came into contact with the dissolution medium. The PFTE loaded holder was placed in the dissolution vessel containing 900 ml of 0.1M of HCl having pH 7.4 at 37±0.5° C. Two pellets were measured for each run of the design of the experiments. Stirring was performed with a paddle rotating at 75 rpm. The dissolution was followed up to 120 min and the concentration of active ingredient, dissolved in the test medium was determined by removing samples of 10 ml at the specified time.

Dissolution Media: 0.01N HCl
RPM: 75
Bowl Temperature: 37° C.
Bath temperature: 37.5° C.
Sample Weight: 200 mg
Sample Preparation: Pellets were prepared by pressing sample with 2 ton pressure for 2 min
Note: Aliquots were analysed on HPLC.

The concentration of (((1-(6-amino-9H-purin-9-yl)propan-2-yloxy)methyl) (phenoxy) phosphoryloxy) methyl pivalate was quantified by HPLC UV method at a maximum wavelength of 300 nm under the conditions as specified below:

| | |
|---|---|
| Mobile Phase | Buffer: Methanol (45:55) Isocratic |
| Buffer | 0.01M Ammonium Acetate in water, pH adjusted to 4.8 with Glacial Acetic Acid |
| Column | Ascentis Express Phenyl Hexyl (10 cm × 4.6 mm × 2.7µ) |
| Column Temp | 35° C. |
| Flow | 1.0 ml/min |
| Injection Volume | 10 µL |
| Diluent | Buffer:Acetonitrile (9:1) |

Standard Preparation: 25 mg standard dissolved to 25 ml with dissolution medium. 5 ml of this solution diluted to 25 ml with dissolution medium. Further 5 ml of this solution was diluted to 10 ml with diluent.

Sample Preparation: 200 mg of Sample pellets were prepared and subjected to dissolution. 10 ml of Aliquot was removed from the dissolution basket at predetermined time intervals. 5 ml of these aliquot was diluted to 10 ml with Diluent.

Example 12—Preparation of Tablet of Fumarate Salt of (((1-(6-amino-9H-purin-9-yl)propan-2-yloxy)methyl) (phenoxy) phosphoryloxy) methyl pivalate 200 mg of input API of fumarate salt of (((1-(6-amino-9H-purin-9-yl)propan-2-yloxy)methyl) (phenoxy) phosphoryloxy) methyl pivalate used for pellet preparation.

Figure 19:
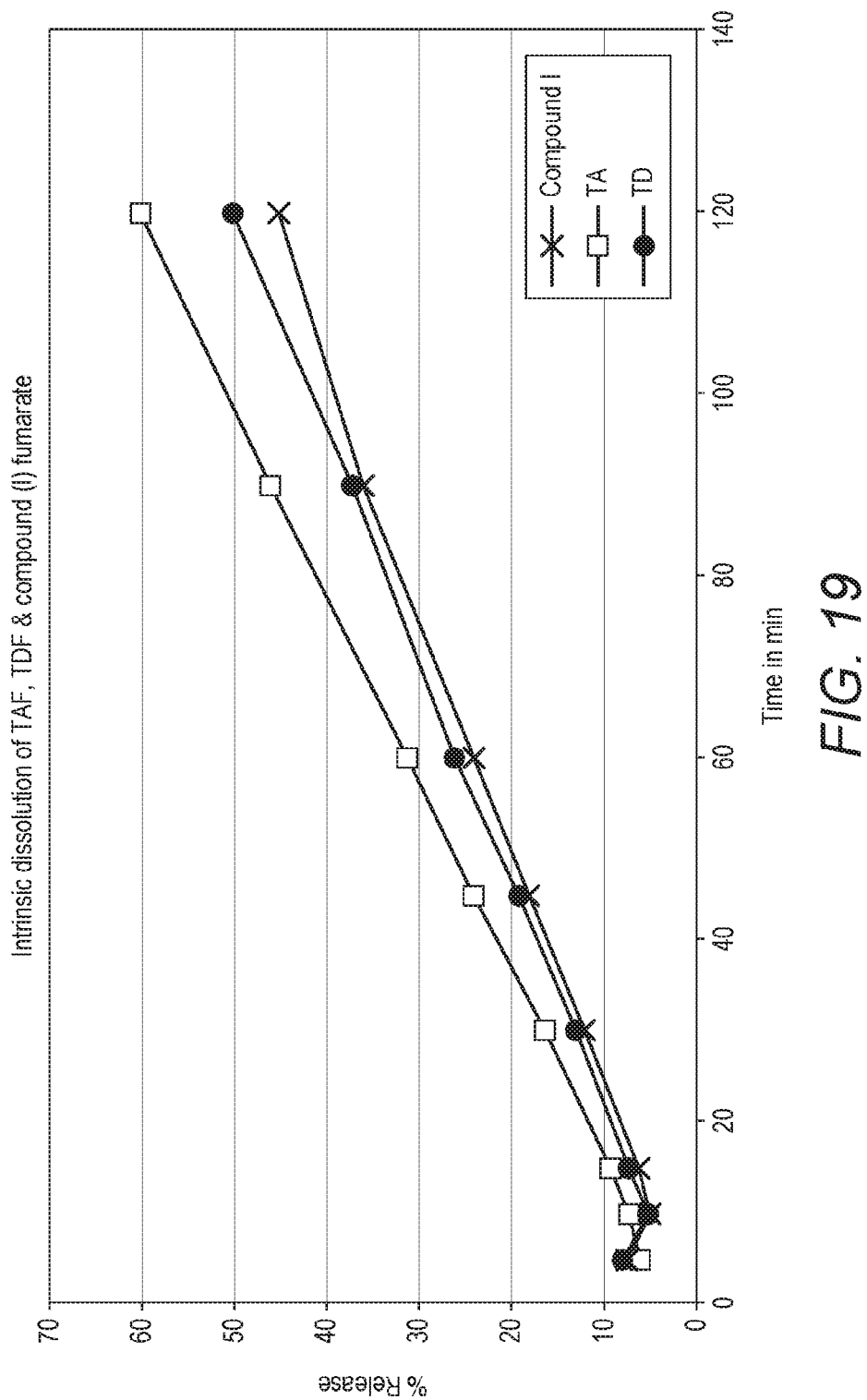
FIG. 19 shows intrinsic dissolution data for the fumarate salt of (((1-(6-amino-9H-purin-9-yl)propan-2-yloxy) methyl)(phenoxy) phosphoryloxy) methyl pivalate compared with that of Tenofovir Disoproxil Fumarate (TDF) and Tenofovir Alafenamide Fumarate (TAF).

The percentage of (((1-(6-amino-9H-purin-9-yl)propan-2-yloxy)methyl) (phenoxy) phosphoryloxy) methyl pivalate (TD), Tenofovir Alafenamide (TAF) and Tenofovir Disoproxil (TDF) released from the respective fumarate salt tablet were plotted against time as shown in FIG. 19. The intrinsic dissolution rate was derived from the slope of this curve. Table 7 shows the results in tabular form. It was observed that the fumarate salt of Compound (I) has slow dissolution profile than TAF and TDF which is shown in table below and hence could be useful in slow released or sustained released formulation.

TABLE 7

Comparison of % release of Compound (I) with TA and TD

| TIME IN MINS | % release of Compound (I) from Fumarate salt of Compound (I) | % release of TA from TAF | % release of TD from TDF |
|---|---|---|---|
| 5 | 7 | 6 | 8 |
| 10 | 5 | 7 | 5 |
| 15 | 6 | 9 | 7 |
| 30 | 12 | 16 | 13 |
| 45 | 18 | 24 | 19 |
| 60 | 24 | 31 | 26 |
| 90 | 35 | 46 | 37 |
| 120 | 45 | 60 | 50 |

Example 13—Preparation of Tablet of Salts of (((1-(6-amino-9H-purin-9-yl)propan-2-yloxy)methyl) (phenoxy) phosphoryloxy) methyl pivalate To measure the intrinsic dissolution of the Salts of (((1-(6-amino-9H-purin-9-yl)propan-2-yloxy)methyl) (phenoxy) phosphoryloxy) methyl pivalate, samples were measured to compare the influence of the different parameter settings. At appropriate time intervals, an automated sample collector removes aliquots from the dissolution medium for analysis. The time interval for sampling can vary, for example, from 5 to 120 minutes, depending on the properties of the drug and dissolution medium used. Suitable dissolution equipment for these operations includes LAB INDIA DISSO 2000. Bath temperature—37.5° C.

200 mg of input API of each fumarate, oxalate, phosphate, citrate, succinate and tartrate Salts of (((1-(6-amino-9H-purin-9-yl)propan-2-yloxy)methyl) (phenoxy) phosphoryloxy) methyl pivalate used for pellet preparation.

The percentage of (((1-(6-amino-9H-purin-9-yl)propan-2-yloxy)methyl) (phenoxy) phosphoryloxy) methyl pivalate released from the respective salts tablet were plotted against time as shown in FIG. 20. The intrinsic dissolution rate was derived from the slope of this curve. Table 8 shows the results in tabular form.

TABLE 8

Comparison of % release of Compound (I) from the respective Salts

| TIME IN MINS | Fumarate | Oxalate | Phosphate | Citrate | Succinate | Tartrate |
|---|---|---|---|---|---|---|
| 5 | 3 | 2 | 19 | 4 | 3 | 2 |
| 15 | 7 | 4 | 59 | 12 | 3 | 6 |
| 30 | 12 | 7 | 103 | 23 | 16 | 12 |
| 45 | 18 | 10 | 104 | 33 | 23 | 17 |
| 60 | 24 | 15 | 105 | 42 | 30 | 24 |
| 90 | 35 | 23 | 105 | 63 | 45 | 35 |
| 120 | 45 | 31 | 106 | 70 | 59 | 47 |
| 150 | 56 | 40 | 105 | 66 | 74 | 59 |
| 180 | 66 | 46 | 104 | 67 | 85 | 70 |
| 210 | 75 | 53 | 104 | 66 | 90 | 80 |
| 240 | 83 | 60 | 105 | 69 | 92 | 88 |

The above data shows that phosphate salt has fastest dissolution profile, compared to other salts. Hence could be useful in an immediate released formulation. Whereas the oxalate salt has the slowest dissolution profile, compared to other salts, and therefore could be useful in a sustained released formulation.

The invention claimed is:

1. A process for preparing (((1-(6-amino-9H-burin-9-yl)propan-2-yloxy) methyl) (phenoxy) phosphoryloxy) methyl pivalate oxalic acid salt in crystalline form and having an XRD pattern comprising peaks at 4.16, 21.30 and 25.7° 2θ #0.2° 2θ or a solvate or hydrate thereof comprising the steps of:
   i) reacting (((1-(6-amino-9H-purin-9-yl)propan-2-yloxy) methyl) (phenoxy) phosphoryloxy) methyl pivalate with oxalic acid in the presence of a solvent selected from isopropyl alcohol, acetone or methanol; and thereafter
   ii) isolating the acid addition salt so formed,
   wherein (((1-(6-amino-9H-purin-9-yl)propan-2-yloxy) methyl) (phenoxy) phosphoryloxy) methyl pivalate oxalic acid salt exhibits dissolution of at least 10% (((1-(6-amino-9H-purin-9-yl)propan-2-yloxy) methyl) (phenoxy) phosphoryloxy) methyl pivalate at 60 minutes or at least 30% of (((1-(6-amino-9H-purin-9-yl)propan-2-yloxy) methyl) (phenoxy) phosphoryloxy) methyl pivalate at 120 minutes in 900 ml of 0.1M of hydrochloric acid having pH 7.4 at 37±0.5° C. with a paddle rotating at 75 revolutions per minute.

2. A process for preparing (((1-(6-amino-9H-purin-9-yl)propan-2-yloxy) methyl) (phenoxy) phosphoryloxy) methyl pivalate tartaric acid salt in crystalline form and having an XRD pattern comprising peaks at 4.73 and 20.65° 2θ±0.2° 2θ or a solvate or hydrate thereof, comprising the steps of:
   i) reacting (((1-(6-amino-9H-purin-9-yl)propan-2-yloxy) methyl) (phenoxy) phosphoryloxy) methyl pivalate with tartaric acid respectively in the presence of a solvent selected from isopropyl alcohol acetone or methanol; and thereafter
   ii) isolating the acid addition salt so formed,
   wherein (((1-(6-amino-9H-purin-9-yl)propan-2-yloxy) methyl) (phenoxy) phosphoryloxy) methyl pivalate tartaric acid salt is-prepared-which-exhibits dissolution of at least 20% of (((1-(6-amino-9H-purin-9-yl)propan-2-yloxy) methyl) (phenoxy) phosphoryloxy) methyl pivalate at 60 minutes or at least 40% of (((1-(6-amino-9H-purin-9-yl)propan-2-yloxy) methyl) (phenoxy) phosphoryloxy) methyl pivalate at 120 minutes in 900 ml of 0.1M of hydrochloric acid having pH 7.4 at 37±0.5° C. with a paddle rotating at 75 revolutions per minute.

3. A process for preparing (((1-{6-amino-9H-purin-9-yl)propan-2-yloxy) methyl} (phenoxy) phosphoryloxy) methyl pivalate fumaric acid salt in crystalline form and having an XRD pattern comprising peaks at 5.03, 23.59 and 29.02° 2θ±0.2° 2θ or a solvate or hydrate thereof, comprising the steps of:
   i) reacting (((1-(6-amino-9H-purin-9-yl)propan-2-yloxy) methyl) (phenoxy) phosphoryloxy) methyl pivalate with fumaric acid in the presence of a solvent selected from isopropyl alcohol, acetone or methanol; and thereafter
   ii) isolating the acid addition salt so formed,
   wherein (((1-(6-amino-9H-purin-9-yl)propan-2-yloxy) methyl) (phenoxy) phosphoryloxy) methyl pivalate fumaric acid salt exhibits dissolution of at least 20% of (((1-(6-amino-9H-purin-9-yl)propan-2-yloxy) methyl) (phenoxy) phosphoryloxy) methyl pivalate at 60 minutes or at least 40% of (((1-(6-amino-9H-purin-9-yl)propan-2-yloxy) methyl) (phenoxy) phosphoryloxy) methyl pivalate at 120 minutes in 900 ml of 0.1M of hydrochloric acid having pH 7.4 at 37±0.5° C. with a paddle rotating at 75 revolutions per minute.

4. A process according to claim 1, wherein the acid salt is isolated by crystallization, precipitation, evaporation or filtration.

5. A process according to claim 2, wherein the acid salt is isolated by crystallization, precipitation, evaporation or filtration.

6. A process according to claim 3, wherein the acid salt is isolated by crystallization, precipitation, evaporation or filtration.

7. A process according to claim 1, wherein step i) is carried out at a temperature between 50-55° C.

8. A process according to claim 1, wherein after step i) the reaction mass is cooled to room temperature.

9. A process according to claim 1, wherein (((1-(6-amino-9H-purin-9-yl)propan-2-yloxy) methyl) (phenoxy) phosphoryloxy) methyl pivalate oxalic acid salt is prepared having an XRD pattern substantially as shown in FIG. 4.

10. A process according to claim 1, wherein (((1-(6-amino-9H-purin-9-yl)propan-2-yloxy) methyl) (phenoxy) phosphoryloxy) methyl pivalate oxalic acid salt is prepared having an IR spectrum comprising peaks at about 3088 cm$^{-1}$, 3185 cm$^{-1}$, 2979 cm$^{-1}$, 1735 cm$^{-1}$, 1693 cm$^{-1}$, 1596 cm$^{-1}$, 1512 cm$^{-1}$, 1491 cm$^{-1}$, 1455 cm$^{-1}$, 1411 cm$^{-1}$, 1368 cm$^{-1}$, 1350 cm$^{-1}$, 1264 cm$^{-1}$, 1229 cm$^{-1}$, 1202 cm$^{-1}$, 1137 cm$^{-1}$, 1071 cm$^{-1}$, 1024 cm$^{-1}$, 994 cm$^{-1}$, 908 cm$^{-1}$, 885 cm$^{-1}$, 820 cm$^{-1}$, 765 cm$^{-1}$, 748 cm$^{-1}$, 716 cm$^{-1}$, 704 cm$^{-1}$ and 689 cm$^{-1}$±2 cm$^{-1}$ or having an IR spectrum substantially as shown in FIG. 5.

11. A process according to claim 1, wherein (((1-(6-amino-9H-purin-9-yl)propan-2-yloxy) methyl) (phenoxy) phosphoryloxy) methyl pivalate oxalic acid salt is prepared having a DSC spectrum having a peak at about 164.9° C. or substantially as shown in FIG. 6.

12. A process according to claim 2, wherein (((1-(6-amino-9H-purin-9-yl)propan-2-yloxy) methyl) (phenoxy) phosphoryloxy) methyl pivalate tartaric acid salt is prepared having an XRD pattern substantially as shown in FIG. 13.

13. A process according to claim 2, wherein (((1-(6-amino-9H-purin-9-yl)propan-2-yloxy) methyl) (phenoxy) phosphoryloxy) methyl pivalate tartaric acid salt is prepared having an IR spectrum comprising peaks at about 3315 $cm^{-1}$, 2975 $cm^{-1}$, 1745 $cm^{-1}$, 1726 $cm^{-1}$, 1679 $cm^{-1}$, 1624 $cm^{-1}$, 1591 $cm^{-1}$ 1489 $cm^{-1}$, 1420 $cm^{-1}$, 1389 $cm^{-1}$, 1324 $cm^{-1}$, 1273 $cm^{-1}$, 1199 $cm^{-1}$, 1141 $cm^{-1}$, 1104 $cm^{-1}$, 1068 $cm^{-1}$, 1025 $cm^{-1}$, 984 $cm^{-1}$, 831 $cm^{-1}$, 806 $cm^{-1}$, 764 $cm^{-1}$, 715 $cm^{-1}$ and 681 $cm^{-1}\pm 2$ $cm^{-1}$ or having an IR spectrum substantially as shown in FIG. 14.

14. A process according to claim 2, wherein (((1-(6-amino-9H-purin-9-yl)propan-2-yloxy) methyl) (phenoxy) phosphoryloxy) methyl pivalate tartaric acid salt is prepared having a DSC spectrum having a peak at about 137.2° C. or substantially as shown in FIG. 15.

15. A process according to claim 3, wherein (((1-(6-amino-9H-purin-9-yl)propan-2-yloxy) methyl) (phenoxy) phosphoryloxy) methyl pivalate fumaric acid salt is prepared having an XRD pattern substantially as shown in FIG. 16.

16. A process according to claim 3, wherein (((1-(6-amino-9H-purin-9-yl)propan-2-yloxy) methyl) (phenoxy) phosphoryloxy) methyl pivalate fumaric acid salt is prepared having an IR spectrum comprising peaks at about 3182 $cm^{-1}$, 3049 $cm^{-1}$, 2976 $cm^{-1}$, 1751 $cm^{-1}$, 1618 $cm^{-1}$, 1489 $cm^{-1}$, 1458 $cm^{-1}$, 1419 $cm^{-1}$, 1395 $cm^{-1}$, 1277 $cm^{-1}$, 1184 $cm^{-1}$, 1098 $cm^{-1}$, 1068 $cm^{-1}$, 980 $cm^{-1}$, 931 $cm^{-1}$, 830 $cm^{-1}$, 787 $cm^{-1}$, 762 $cm^{-1}$, 723 $cm^{-1}$ and 687 $cm^{-1}\pm 2$ $cm^{-1}$ or having an IR spectrum substantially as shown in FIG. 17.

17. A process according to claim 3, wherein (((1-(6-amino-9H-purin-9-yl)propan-2-yloxy) methyl) (phenoxy) phosphoryloxy) methyl pivalate fumaric acid salt is prepared having a DSC spectrum having a peak at about 119.8° C. or substantially as shown in FIG. 18.

18. A process according to claim 2, wherein step i) is carried out at a temperature between 50-55° C.

19. A process according to claim 2, wherein after step i) the reaction mass is cooled to room temperature.

20. A process according to claim 3, wherein step i) is carried out at a temperature between 70-75° C.

21. A process according to claim 3, wherein after step i) the reaction mass is cooled to room temperature.

* * * * *